(12) United States Patent
Kosuge et al.

(10) Patent No.: US 9,240,553 B2
(45) Date of Patent: Jan. 19, 2016

(54) INDENO[1,2-B]PHENANTHRENE COMPOUND AND ORGANIC LIGHT EMITTING ELEMENT INCLUDING THE SAME

(71) Applicant: CANON KABUSHIKI KAISHA, Tokyo (JP)

(72) Inventors: Tetsuya Kosuge, Yokohama (JP); Naoki Yamada, Inagi (JP); Jun Kamatani, Tokyo (JP); Kengo Kishino, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/433,009

(22) PCT Filed: Sep. 10, 2013

(86) PCT No.: PCT/JP2013/074958
§ 371 (c)(1),
(2) Date: Apr. 1, 2015

(87) PCT Pub. No.: WO2014/054410
PCT Pub. Date: Apr. 10, 2014

(65) Prior Publication Data
US 2015/0255727 A1 Sep. 10, 2015

(30) Foreign Application Priority Data

Oct. 5, 2012 (JP) ................. 2012-222890

(51) Int. Cl.
| | |
|---|---|
| *H01L 51/00* | (2006.01) |
| *H05B 33/08* | (2006.01) |
| *H01L 27/32* | (2006.01) |
| *G03G 15/04* | (2006.01) |
| *C07C 13/62* | (2006.01) |
| *C07C 43/21* | (2006.01) |
| *C07C 255/52* | (2006.01) |
| *C07C 13/66* | (2006.01) |
| *C07D 333/76* | (2006.01) |
| *C07D 307/91* | (2006.01) |
| *C07D 209/86* | (2006.01) |
| *C07D 215/06* | (2006.01) |
| *H01L 51/50* | (2006.01) |

(52) U.S. Cl.
CPC ............ *H01L 51/0055* (2013.01); *C07C 13/62* (2013.01); *C07C 13/66* (2013.01); *C07C 43/21* (2013.01); *C07C 255/52* (2013.01); *C07D 209/86* (2013.01); *C07D 215/06* (2013.01); *C07D 307/91* (2013.01); *C07D 333/76* (2013.01); *G03G 15/04036* (2013.01); *H01L 27/3244* (2013.01); *H01L 51/0058* (2013.01); *H01L 51/0072* (2013.01); *H01L 51/0073* (2013.01); *H01L 51/0074* (2013.01); *H05B 33/0896* (2013.01); *C07C 2103/52* (2013.01); *H01L 51/5024* (2013.01)

(58) Field of Classification Search
CPC .................................................. H01L 51/0055
USPC ........................................................ 546/173
See application file for complete search history.

(56) References Cited

U.S. PATENT DOCUMENTS

| 6,358,633 | B1 | 3/2002 | Sano |
| 2004/0076853 | A1 | 4/2004 | Jarikov |

FOREIGN PATENT DOCUMENTS

| CN | 1226319 A | 8/1999 |
| CN | 1764708 A | 4/2006 |
| KR | 10-2012-0122897 A | 11/2012 |
| WO | 98/51757 A1 | 11/1998 |

*Primary Examiner* — Taofiq A Solola
(74) *Attorney, Agent, or Firm* — Canon U.S.A. Inc., IP Division

(57) ABSTRACT

The present invention provides an indeno[1,2-b]phenanthrene compound having suppressed hole transport ability. The indeno[1,2-b]phenanthrene compound represented by the general formula [1] described in claim 1 is provided. In the formula [1], $R_1$ and $R_2$ each represent a hydrogen atom or an alkyl group. $X_1$ and $X_2$ each represent a substituent selected from the group consisting of a hydrogen atom, an alkyl group, a methoxy group, and a cyano group. $A_1$ represents a monovalent or a divalent aromatic hydrocarbon group. $A_2$ represents a monovalent or a divalent aromatic hydrocarbon group or a monovalent or a divalent heteroaromatic group. n represents an integer of 0 to 4. When n is 2 or more, a plurality of $A_2$ may be identical to or different from each other.

16 Claims, 2 Drawing Sheets

INDENO[1,2-B]PHENANTHRENE COMPOUND AND ORGANIC LIGHT EMITTING ELEMENT INCLUDING THE SAME

TECHNICAL FIELD

The present invention relates to an indeno[1,2-b]phenanthrene compound and an organic light emitting element including the same.

BACKGROUND ART

An organic light emitting element is an electronic element having an anode, a cathode, and an organic compound layer provided between those electrodes. In the organic light emitting element, holes and electrons, which are injected from the respective electrodes, are recombined with each other in the organic compound layer to generate excitons, and when the excitons are returned to the ground state, light is emitted. Recent advancement of organic light emitting elements has been significant, and thin and lightweight light emitting devices having a low drive voltage, various light emitting wavelengths, and a high speed responsibility can be achieved.

Among the organic light emitting elements, a phosphorescent light emitting element is a light emitting element which includes a phosphorescent light emitting material in an organic compound layer and which can emit light derived from triplet excitons. However, the light emitting efficiency and durability life of the phosphorescent light emitting element are still required to be improved, and in particular, improvement in carrier balance in a light emitting layer has been desired.

As one fused polycyclic aromatic hydrocarbon compound used as a constituent material of the organic compound layer, indeno[1,2-b]phenanthrene (also called "1',2'-naphtha-2,3-fluorene") may be mentioned. In PTL 1 has disclosed that the following non-substituted compound is used as a fluorescent light emitting dopant.

[Chem.1]

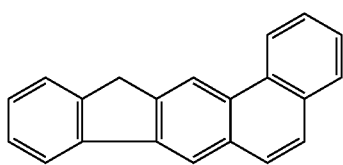

However, the non-substituted indeno[1,2-b]phenanthrene proposed in PTL 1 has a high planarity, and hence, the intermolecular stack is intensive. In addition, since having a small molecular size, the non-substituted indeno[1,2-b]phenanthrene has a low glass transition temperature. Hence, an organic light emitting element in which the non-substituted indeno[1,2-b]phenanthrene is introduced into a host of a light emitting layer may not have an excellent element performance.

CITATION LIST

Patent Literature

PTL 1 International Publication No. WO98/51757

SUMMARY OF INVENTION

The present invention is to solve the above problem and provides an indeno[1,2-b]phenanthrene compound having a suppressed hole transport ability. In addition, the present invention also provides an organic light emitting element having an excellent element life performance.

The indeno[1,2-b]phenanthrene compound of the present invention is a compound represented by the following formula [1].

[Chem. 2]

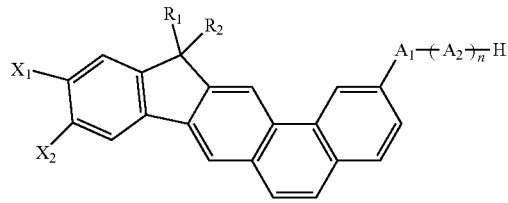

[1]

In the formula [1], $R_1$ and $R_2$ each represent a hydrogen atom or an alkyl group. $X_1$ and $X_2$ each represent a substituent selected from the group consisting of a hydrogen atom, an alkyl group, a methoxy group, and a cyano group. $A_1$ represents a monovalent or a divalent aromatic hydrocarbon group. In addition, $A_1$ is optionally substituted by an alkyl group, a phenyl group optionally further substituted by an alkyl group, or a biphenyl group optionally further substituted by an alkyl group. $A_2$ represents a monovalent or a divalent aromatic hydrocarbon group or a monovalent or a divalent heteroaromatic group. In addition, $A_2$ is optionally substituted by an alkyl group, a phenyl group optionally further substituted by an alkyl group, or a biphenyl group optionally further substituted by an alkyl group. n represents an integer of 0 to 4. When n is 2 or more, a plurality of $A_2$ may be identical to or different from each other.

ADVANTAGEOUS EFFECTS OF INVENTION

According to the present invention, an indeno[1,2-b]phenanthrene compound having suppressed hole transport ability can be provided. That is, the indeno[1,2-b]phenanthrene compound of the present invention is a compound which contributes to improve the carrier balance in a light emitting layer. In addition, according to the present invention, an organic light emitting element having an excellent element life performance can be provided.

Further features of the present invention will become apparent from the following description of exemplary embodiments with reference to the attached drawings.

DESCRIPTION OF EMBODIMENTS

Indeno[1,2-b]Phenanthrene Compound

Figure 1:
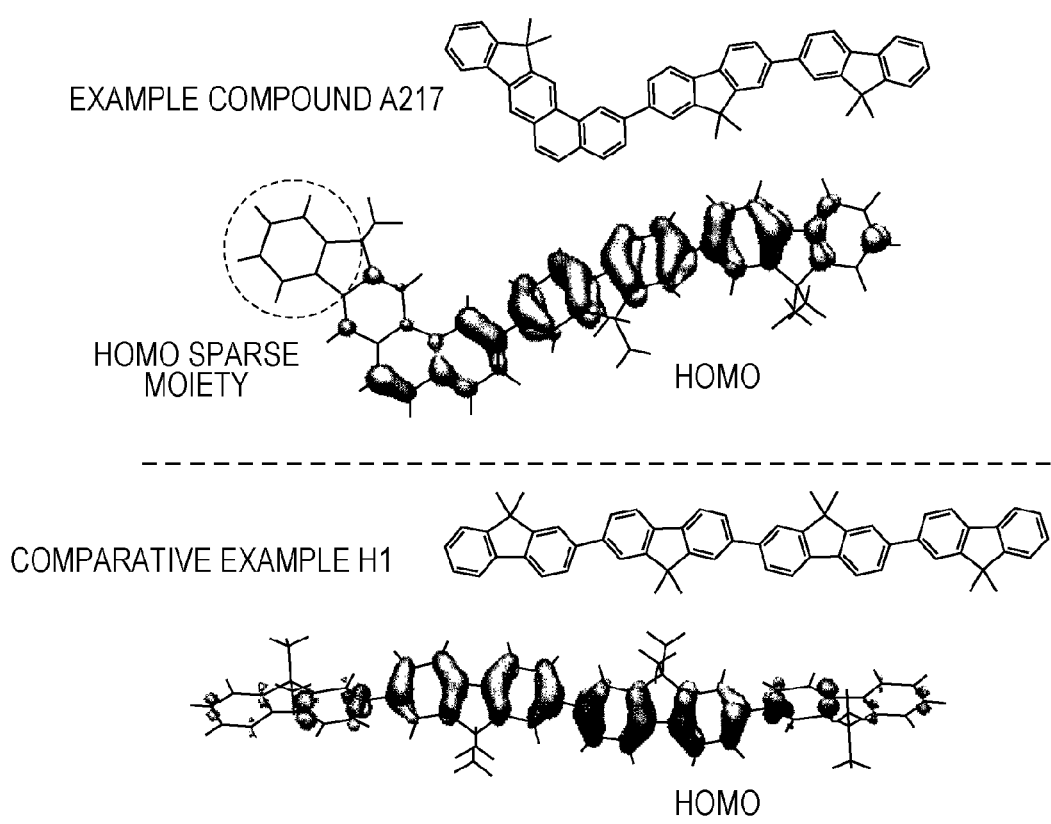
FIG. 1 is a schematic view showing the HOMO of an example compound A217 and the HOMO of a comparative compound H1.

First, an indeno[1,2-b]phenanthrene compound of the present invention will be described. The indeno[1,2-b]

phenanthrene compound of the present invention is a compound represented by the following general formula [1].

[Chem. 3]

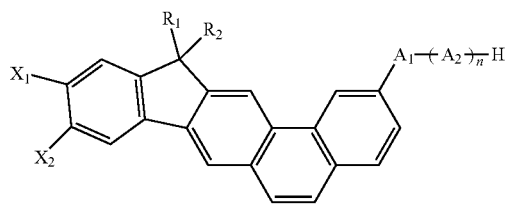

[1]

In the formula [1], $R_1$ and $R_2$ each represent a hydrogen atom or an alkyl group. In the present invention, the alkyl group is a linear, a branched, or a cyclic alkyl group functioning as a saturated hydrocarbon substitute.

As specific examples of the alkyl group represented by $R_1$ and $R_2$, for example, there may be mentioned a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a n-hexyl group, a cyclohexyl group, and a n-dodecyl group.

As the alkyl group represented by $R_1$ and $R_2$, an alkyl group having 1 to 4 carbon atoms is preferable, and a methyl group is more preferable.

In the formula [1], $X_1$ and $X_2$ each represent a substituent selected from the group consisting of a hydrogen atom, an alkyl group, a methoxy group, and a cyano group. $X_1$ and $X_2$ each preferably represent a hydrogen atom.

Specific examples of the alkyl group represented by $X_1$ and $X_2$ are similar to the specific examples of the alkyl group represented by $R_1$ and $R_2$.

As the alkyl group represented by $X_1$ and $X_2$, an alkyl group having 1 to 4 carbon atoms is preferable, and a methyl group or a tert-butyl group is more preferable.

In the formula [1], $A_1$ represents a monovalent or a divalent aromatic hydrocarbon group. In particular, when n, which will be described later, is 0, $A_1$ represents a monovalent aromatic hydrocarbon group, and when n is 1 or more, $A_1$ represents a divalent aromatic hydrocarbon group. In the present invention, the aromatic hydrocarbon group indicates an aromatic group which is formed only from carbon atoms and hydrogen atoms and which includes no hetero atoms.

When $A_1$ represents a monovalent aromatic hydrocarbon group, as specific examples of the aromatic hydrocarbon group represented by $A_1$, for example, there may be mentioned a phenyl group, a naphthyl group, a phenanthryl group, an anthryl group, a benzo[a]anthryl group, a fluorenyl group, a benzo[a]fluorenyl group, a benzo[b]fluorenyl group, a benzo[c]fluorenyl group, a dibenzo[a,c]fluorenyl group, a dibenzo[b,h]fluorenyl group, a dibenzo[c,g]fluorenyl group, a biphenylenyl group, an acenaphthylenyl group, a chrysenyl group, a benzo[b]chrysenyl group, a pyrenyl group, a benzo[e]pyrenyl group, a triphenylenyl group, a benzo[a]triphenylenyl group, a benzo[b]triphenylenyl group, a picenyl group, a fluoranthenyl group, a benzo[a]fluoranthenyl group, a benzo[b]fluoranthenyl group, a benzo[j]fluoranthenyl group, a benzo[k]fluoranthenyl group, a perylenyl group, and a naphthacenyl group.

When $A_1$ represents a divalent aromatic hydrocarbon group, as specific examples of the aromatic hydrocarbon group represented by $A_1$, for example, there may be mentioned a phenylene group, a naphthalenediyl group, a phenanthrenediyl group, an anthracenediyl group, a benzo[a]anthracenediyl group, a fluorenediyl group, a benzo[a]fluorenediyl group, a benzo[b]fluorenediyl group, a benzo[c]fluorenediyl group, a dibenzo[a,c]fluorenediyl group, a dibenzo[b,h]fluorenediyl group, a dibenzo[c,g]fluorenediyl group, a biphenylenediyl group, an acenaphthylenediyl group, a chrysenediyl group, a benzo[b]chrysenediyl group, a pyrenediyl group, a benzo[e]pyrenediyl group, a triphenylenediyl group, a benzo[a]triphenylenediyl group, a benzo[b]triphenylenediyl group, a picenediyl group, a fluoranthenediyl group, a benzo[a]fluoranthenediyl group, a benzo[b]fluoranthenediyl group, a benzo[j]fluoranthenediyl group, a benzo[k]fluoranthenediyl group, a perylenediyl group, and a naphthacenediyl group.

In addition, in the present invention, the substitute represented by $A_1$ may further have as a substitute, an alkyl group, a phenyl group which may be substituted by an alkyl group, or a biphenyl group which may be substituted by an alkyl group. In particular, the alkyl group described above is similar to the alkyl group represented by $R_1$ and $R_2$, and specific examples of the alkyl group are similar to those of the alkyl group represented by $R_1$ and $R_2$. In addition, as the alkyl group functioning as the substitute (including the alkyl group forming a part of the substituent) that the substituent represented by $A_1$ may further have, an alkyl group having 1 to 4 carbon atoms is preferable, and a methyl group or a tert-butyl group is more preferable.

In the formula [1], $A_2$ represents a monovalent or a divalent aromatic hydrocarbon group or a monovalent or a divalent heteroaromatic group. The heteroaromatic group described above indicates an aromatic group including carbon atoms, hydrogen atoms, and at least one hetero atom (atom other than a carbon atom and a hydrogen atom).

Specific examples of the monovalent aromatic hydrocarbon group represented by $A_2$ are similar to the specific examples of the above $A_1$. In addition, specific examples of the divalent aromatic hydrocarbon group represented by $A_2$ are also similar to the specific examples of the above $A_1$.

As specific examples of the monovalent heteroaromatic group represented by $A_2$, for example, there may be mentioned a thienyl group, a pyrrolyl group, a pyrazinyl group, a pyridyl group, an indolyl group, a quinolyl group, an isoquinolyl group, a naphthyridinyl group, an acridinyl group, a phenanthroliny group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, an oxadiazolyl group, an indeno[3,2,1-kl]phenoxazinyl group, and an indeno[3,2,1-jk]carbazolyl group.

As specific examples of the divalent heteroaromatic group represented by $A_2$, for example, there may be mentioned a thiophenediyl group, a pyrrolediyl group, a pyrazinediyl group, a pyridinediyl group, an indolediyl group, a quinolinediyl group, an isoquinolinediyl group, a naphthyridinediyl group, an acridinediyl group, a phenanthrolinediyl group, a carbazolediyl group, a benzo[a]carbazolediyl group, a benzo[b]carbazolediyl group, a benzo[c]carbazolediyl group, a phenazinediyl group, a phenoxazinediyl group, a phenothiazinediyl group, a benzothiophenediyl group, a dibenzothiophenediyl group, a benzofurandiyl group, a dibenzofurandiyl group, an oxazolediyl group, an oxadiazolediyl group, an indeno[3,2,1-kl]phenoxazinediyl group, and an indeno[3,2,1-jk]carbazolediyl group.

In addition, in the present invention, the substitute represented by $A_2$ may further have as a substituent, an alkyl group, a phenyl group which may be substituted by an alkyl group, or a biphenyl group which may be substituted by an alkyl group. In particular, the alkyl group described above is similar to the alkyl group represented by $R_1$ and $R_2$, and specific examples of the alkyl group are similar to those of the alkyl group represented by $R_1$ and $R_2$. In addition, as the alkyl group functioning as the substitute (including the alkyl group forming a part of the substituent) that the substituent represented by $A_2$ may further have, an alkyl group having 1 to 4 carbon atoms is preferable, and a methyl group or a tert-butyl group is more preferable.

In the formula [1], n represents an integer of 0 to 4. n is preferably 0 or 1 and more preferably 1. When n is 2 or more, a plurality of $A_2$ may be identical to or different from each other.

The indeno[1,2-b]phenanthrene compound of the present invention is particularly preferably an indeno[1,2-b]phenanthrene compound represented by the following general formula [2].

[Chem. 4]

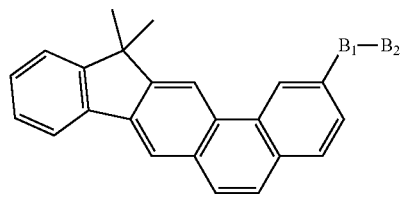

[2]

In the formula [2], $B_1$ represents a divalent aromatic hydrocarbon group.

Specific examples of the divalent aromatic hydrocarbon group represented by $B_1$ are similar to those of the divalent aromatic hydrocarbon group represented by the above $A_1$.

In addition, $B_1$ may further have an alkyl group as a substitute. Specific examples of the alkyl group that $B_1$ may further have are similar to those of the alkyl group represented by the above $R_1$ and $R_2$. The alkyl group that $B_1$ may further have is preferably an alkyl group having 1 to 4 carbon atoms and more preferably a methyl group or a tert-butyl group.

In the formula [2], $B_2$ represents a monovalent aromatic hydrocarbon group or a monovalent heteroaromatic group.

Specific examples of the monovalent aromatic hydrocarbon group represented by $B_2$ are similar to those of the monovalent aromatic hydrocarbon group represented by the above $A_1$.

Specific examples of the monovalent heteroaromatic group represented by $B_2$ are similar to those of the monovalent heteroaromatic group represented by the above $A_2$.

In addition, $B_2$ may further have an alkyl group as a substituent. Specific examples of the alkyl group that $B_2$ may further have are similar to those of the alkyl group represented by the above $R_1$ and $R_2$. The alkyl group that $B_2$ may further have is preferably an alkyl group having 1 to 4 carbon atoms and more preferably a methyl group or a tert-butyl group.

The indeno[1,2-b]phenanthrene compound represented by the formula [2] is more preferably a compound in which $B_1$ in the formula [2] is selected from the following divalent substituent group.

[Chem. 5]

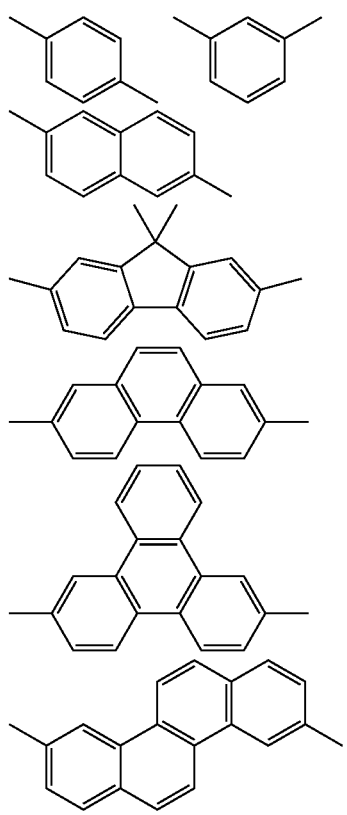

Synthetic Method of Compound

Next, a synthetic method of the indeno[1,2-b]phenanthrene compound of the present invention will be described.

The indeno[1,2-b]phenanthrene compound of the present invention is synthesized, for example, in accordance with a synthetic scheme represented by the following general formula [3].

[Chem. 6]

[3]

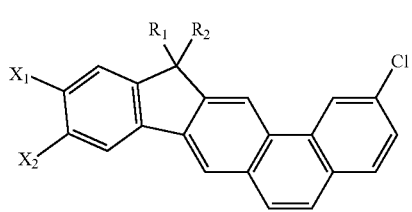 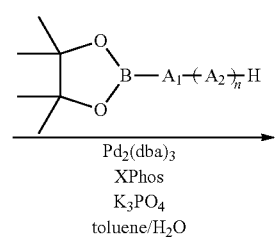

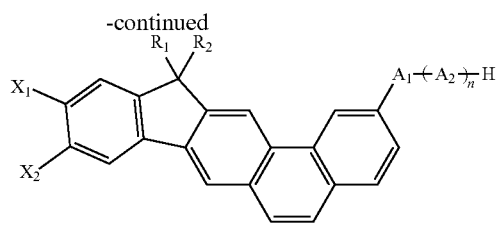

In the formula [3], $R_1$, $R_2$, $X_1$, $X_2$, $A_1$, $A_2$, and n are the same as $R_1$, $R_2$, $X_1$, $X_2$, $A_1$, $A_2$, and n of the general formula [1], respectively.

In particular, the synthesis can be performed by a cross-coupling reaction with a Pd catalyst using the following compounds (A) and (B).
(A) A compound in which the 2-position of indeno[1,2-b]phenanthrene is substituted by a chlorine atom.
(B) A pinacol borane ester compound having a substituent represented by $A_1$-$(A_2)_n$-H.

However, instead of the compounds (A) and (B), the following compounds (A') and (B') may also be used.
(A') A compound in which the 2-position of indeno[1,2-b]phenanthrene is substituted by a pinacol borane ester group.
(B') A compound represented by Hal-$A_1$-$(A_2)_n$-H (Hal: a halogen atom).

For example, the compound (A) may be synthesized in accordance with a synthetic scheme represented by the following formula [4].

[Chem. 7]

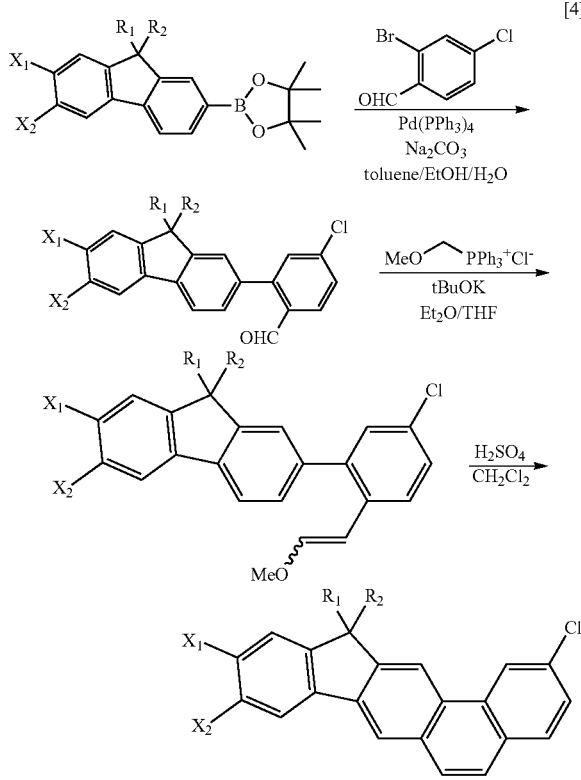

[4]

In the formula [4], $R_1$, $R_2$, $X_1$, and $X_2$ are the same as $R_1$, $R_2$, $X_1$, and $X_2$ of the general formula [1], respectively.

In particular, the synthesis can be carried out by sequentially performing the following reactions (1) to (3) using a pinacol boronate ester of a fluorene having desired substituents $R_1$, $R_2$, $X_1$, and $X_2$ and 2-bromo-4-chlorobenzaldehyde as starting raw materials.
(1) A cross-coupling reaction using a Pd catalyst
(2) Wittig reaction
(3) Oxidation cyclization reaction Properties of Compound In general, in an organic light emitting element, as one cause that decreases the light emitting efficiency and/or degrades the durability life, localization of light emitting region (carrier recombination region) in a light emitting layer may be mentioned. When the carrier balance between holes and electrons to be supplied in the light emitting layer is not well maintained since one type of carriers is supplied too much or too small, the localization of light emitting region is liable to occur. In this case, since the two types of carriers are not sufficiently transported inside the light emitting layer, local light emission unfavorably occurs in the vicinity of the interface between a carrier transport layer and the light emitting layer.

Accordingly, in order to achieve a high efficiency and a longer life of the organic light emitting element, the carrier balance between holes and electrons in the light emitting layer has to be improved to expand the light emitting region. In order to improve the carrier balance, when the supply of carriers is taken into consideration, it is important to adjust both the amount of carriers to be injected into the light emitting layer and the amount of carriers to be transported in the light emitting layer. In this case, in a common organic light emitting element in which the light emitting layer is formed of a light emitting guest and a host, it is necessary that as for the host, a carrier injection property be adjusted by the HOMO level and the LUMO level, and a carrier transport property be adjusted by the hole mobility and the electron mobility.

In general, in many hosts contained in the light emitting layer, since the HOMO level of the host is deeper (higher ionization potential) than the HOMO level of an adjacent hole transport layer, although the hole injection property is low, the hole mobility of the host is relatively high. Hence, it may be said that the hole transport property is high. Accordingly, when the organic light emitting element is driven, since a small amount of injected holes rapidly travels in the light emitting layer and is transported to an electron transport layer side, the carrier supply balance is degraded, and as a result, the localization of the light emitting region is liable to occur.

In particular, in a phosphorescent light emitting element using a phosphorescent light emitting material as a light emitting guest, the carrier balance described above is particularly liable to degrade. The reason for this is that in general, since the HOMO level of a host contained in a phosphorescent light emitting layer is deep in many cases, in particular, the hole injection property from the hole transport layer is low, and at the same time, the hole mobility is more increased.

Hence, in order to improve the carrier balance, the hole transport property may be decreased by decreasing the hole mobility of the host so as to improve the balance with a low hole injection property. As a method in which the hole mobility of the host is decreased in an amorphous film such as the light emitting layer forming the organic light emitting element, a method may be mentioned in which the orbital overlap in HOMO between molecules is decreased to increase a hopping distance of holes. By the method as described above, the hole mobility can be decreased.

Accordingly, the present inventor aimed to decrease the HOMO distribution on the molecule by providing a HOMO sparse moiety in each molecular structure so as to decrease the orbital overlap in HOMO between molecules. In this case, the HOMO sparse moiety indicates a moiety in which the orbital density of the HOMO is low in the molecular structure or a moiety on which the HOMO does not reside. In addition, the present inventor found that the indeno[1,2-b]phenanthrene compound of the present invention is a compound in which the HOMO sparse moiety as described above can be provided.

In this embodiment, the HOMO of a compound (example compound A217) which is the indeno[1,2-b]phenanthrene of the present invention and the HOMO of an oligofluorene compound (comparative compound H1) having a structure similar to that of the above compound will be discussed.

FIG. 1 is a schematic view showing the HOMO of the example compound A217 and the HOMO of the comparative compound H1.

In the example compound A217 which is the indeno[1,2-b]phenanthrene of the present invention, a HOMO sparse moiety is present at an indeno moiety of the indeno[1,2-b]phenanthrene ring located at a molecular end. On the other hand, no HOMO sparse moiety is present in the comparative compound H1 unlike the case of the example compound A217, and the HOMO uniformly extends.

As shown in FIG. 1, the reason the HOMO sparse moiety is present in the example compound A217 is that the example compound A217 has a specific molecular structure in which a hydrogen atom bonded to the carbon atom at the 2-position of the indeno[1,2-b]phenanthrene skeleton is substituted by an aromatic hydrocarbon group (fluorenyl group). Incidentally, on the indeno[1,2-b]phenanthrene skeleton, 13 substitution sites are present as shown in the following chemical formula.

[Chem. 8]

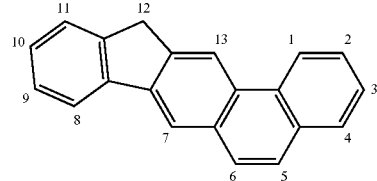

When molecular orbital calculation is performed on the compound in which a hydrogen atom at each of the 13 substitution sites of the indeno[1,2-b]phenanthrene skeleton is substituted by a phenyl group functioning as the aromatic hydrocarbon group, the HOMO of each compound is as shown in the following Table 1. In addition, as for the 1-position substitution product, since the steric interference between the phenyl group and the hydrogen atom at the 13-position is high, a stable structure cannot be obtained, and hence the 1-position substitution product is omitted in Table 1. The 13-position substitution product is also omitted by the same reason as that of the 1-position substitution product. In addition, since the carbon at the 12-position is a $sp_3$ carbon, the π conjugation is not formed between the phenyl group and the indeno[1,2-b]phenanthrene skeleton, and hence, the 12-position substitution product is also omitted.

TABLE 1

| SUBSTITUTION SITE | STRUCTURAL FORMULA | HOMO |
|---|---|---|
| 2-POSITION | | HOMO SPARSE MOIETY |
| 3-POSITION | | |

TABLE 1-continued
| SUBSTITUTION SITE | STRUCTURAL FORMULA | HOMO |
|---|---|---|
| 4-POSITION | 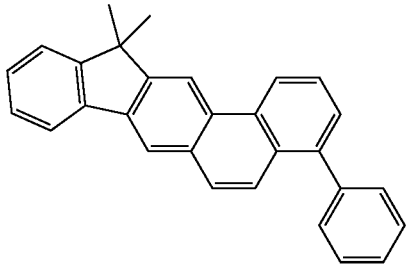 [SMILES: CC1(C)c2ccccc2-c2cc3ccc4c(-c5ccccc5)cccc4c3cc21] |  |
| 5-POSITION | 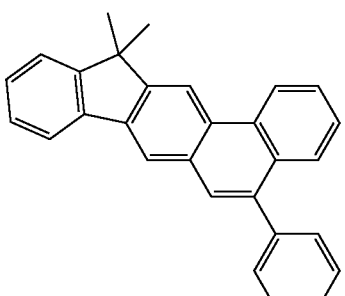 | 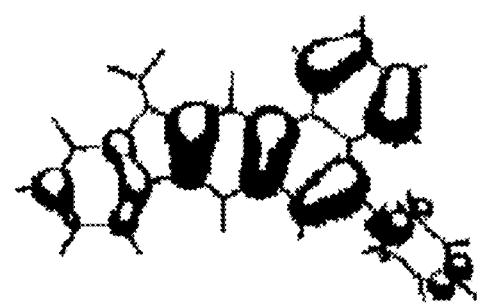 |
| 6-POSITION | 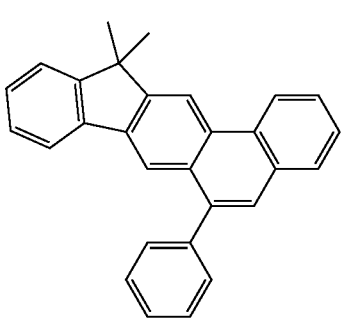 [SMILES: CC1(C)c2ccccc2-c2cc3c(-c4ccccc4)cc4ccccc4c3cc21] | 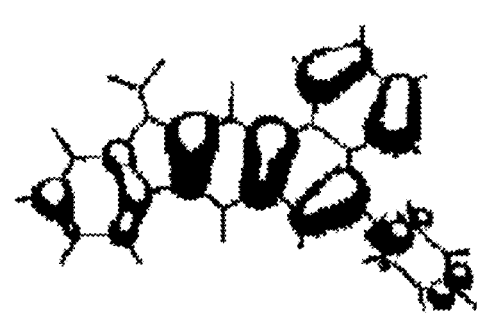 |
| 7-POSITION | 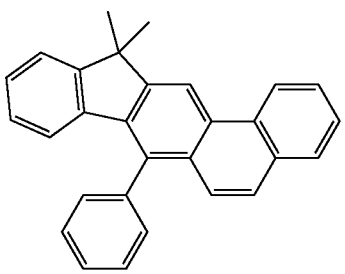 [SMILES: CC1(C)c2ccccc2-c2c1cc1c(ccc3ccccc31)c2-c1ccccc1] |  |
| 8-POSITION | 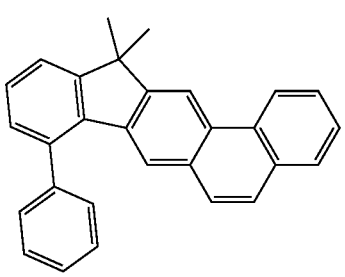 [SMILES: CC1(C)c2cc3c(ccc4ccccc43)cc2-c2c(-c3ccccc3)cccc21] | 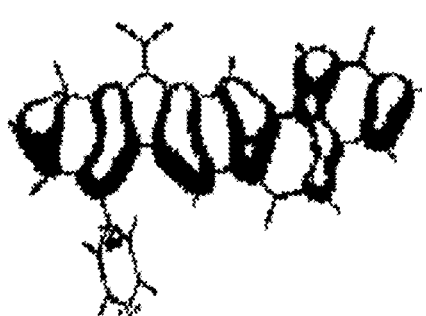 |

TABLE 1-continued

| SUBSTITUTION SITE | STRUCTURAL FORMULA | HOMO |
|---|---|---|
| 9-POSITION | | |
| 10-POSITION | | |
| 11-POSITION | | |

From Table 1, it is found that only when a hydrogen atom bonded to the carbon atom at the 2-position of the indeno[1,2-b]phenanthrene skeleton is substituted by a phenyl group, a HOMO sparse moiety is formed. In addition, when molecular orbital calculation was also performed on a compound in which a hydrogen atom bonded to the carbon atom at the 2-position of the indeno[1,2-b]phenanthrene skeleton is substituted by an aromatic hydrocarbon group (such as a naphthyl group or a fluorenyl group) other than a phenyl group, the presence of a HOMO sparse moiety similar to that described above could also be confirmed. Hence, as long as a hydrogen atom bonded to the carbon atom at the 2-position of the indeno[1,2-b]phenanthrene skeleton is substituted, regardless of the type of aromatic hydrocarbon group functioning as a substituent, it can be said that a HOMO sparse moiety is present in the indeno[1,2-b]phenanthrene compound.

As described above, when a hydrogen atom bonded to the carbon atom at the 2-position of the indeno[1,2-b]phenanthrene skeleton is substituted by an aromatic hydrocarbon group, the indeno[1,2-b]phenanthrene compound of the present invention has a HOMO sparse moiety at a molecular end. Accordingly, since the indeno[1,2-b]phenanthrene compound of the present invention has a low hole transport property, if the indeno[1,2-b]phenanthrene compound is used as the host of the light emitting layer of the organic light emitting element, the carrier balance in the light emitting layer is improved. Hence, in an organic light emitting element including the indeno[1,2-b]phenanthrene compound of the present invention, the light emitting efficiency and the life are improved.

Furthermore, $T_1$ (minimum triplet excited state) energy in wavelength of the indeno[1,2-b]phenanthrene itself is 481 nm. Accordingly, the indeno[1,2-b]phenanthrene compound of the present invention is preferably used as the host in the light emitting layer when a red phosphorescent light emitting material is used as the guest. In this case, the red phosphorescent light emitting material is a phosphorescent light emitting material in which the maximum light emitting peak wavelength of a phosphorescent light emitting spectrum in a diluted solution is in a range of 580 to 630 nm.

However, when the indeno[1,2-b]phenanthrene compound of the present invention is used as the host for the red phosphorescent light emitting material (guest), an aromatic ring having $T_1$ energy in wavelength of more than approximately 540 nm must not be introduced in the indeno[1,2-b]phenanthrene compound. The reason for this is that the $T_1$ energy of the host must be set to be larger than that of the guest so as not to quench $T_1$ excitons in the light emitting layer. In the following Table 2, the $T_1$ energies (in wavelength) of main aromatic rings are shown.

TABLE 2

| | STRUCTURAL FORMULA | $T_1$ ENERGY IN WAVELENGTH/nm |
|---|---|---|
| BENZENE | | 339 |
| CARBAZOLE | | 407 |
| DIBENZOTHIOPHENE | | 415 |
| DIBENZOFURAN | | 417 |
| FLUORENE | | 422 |
| TRIPHENYLENE | | 427 |
| BIPHENYL | | 438 |
| PHENANTHROLINE | | 453 |
| PHENOXAZINE | | 456 |
| ANTHRAQUINONE | | 458 |
| PHENANTHRENE | | 459 |

TABLE 2-continued

| | STRUCTURAL FORMULA | $T_1$ ENERGY IN WAVELENGTH/nm |
|---|---|---|
| INDOLOPHENOXAZINE | | 460 |
| QUINOLINE | | 464 |
| NAPHTHALENE | | 472 |
| INDENO[1,2-B] PHENANTHRENE | | 481 |
| PICENE | | 498 |
| CHRYSENE | | 500 |
| FLUORANTHENE | | 541 |
| BENZO[k]FLUORANTHENE | | 567 |
| PYRENE | | 589 |
| ANTHRACENE | | 672 |

TABLE 2-continued

| | STRUCTURAL FORMULA | $T_1$ ENERGY IN WAVELENGTH/nm |
|---|---|---|
| PERYLENE | | 808 |

From Table 2, an indeno[1,2-b]phenanthrene compound which is formed only from an aromatic ring (benzene to chrysene) having a $T_1$ energy higher than that of indeno[1,2-b]phenanthrene is preferably used as the host of the light emitting layer when the red phosphorescent light emitting material is used as the guest.

In addition, the indeno[1,2-b]phenanthrene compound of the present invention may also be used as the host of the light emitting layer when a fluorescent light emitting material is used as the guest. In this case, although an indeno[1,2-b]phenanthrene compound having a $S_1$ energy suitable for a light emitting wavelength of the fluorescent light emitting material must be appropriately selected, the restriction of the $T_1$ energy described above is not necessarily taken into consideration. Hence, an indeno[1,2-b]phenanthrene compound which includes an aromatic ring having a lower $T_1$ energy than that of indeno[1,2-b]phenanthrene itself may also be used as the host of the light emitting layer for the fluorescent light emitting material (guest).

In addition, when the indeno[1,2-b]phenanthrene compound of the present invention is used as a constituent material of the organic light emitting element, the purity of the indeno[1,2-b]phenanthrene compound is preferably increased immediately before the use thereof by sublimation purification or the like. The reason for this is that for high purification of organic compounds, the sublimation purification has an excellent purification effect. In the sublimation purification as described above, in general, a higher molecular weight organic compound requires a higher temperature, and by this higher temperature, for example, the organic compound is liable to be thermally decomposed. Hence, an organic compound used as the constituent material of the organic light emitting element preferably has a molecular weight of 1,000 or less so that the sublimation purification may be carried out without performing excessive heating.

Specific Examples of Indeno[1,2-b]Phenanthrene Compound

Hereinafter, specific examples of the indeno[1,2-b]phenanthrene compound of the present invention will be shown. However, the present invention is not limited to those examples.

[Chem. 9]

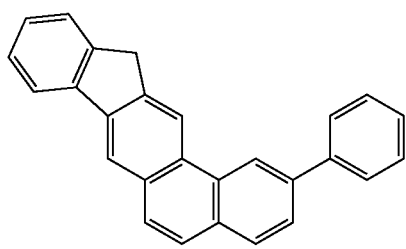

A101

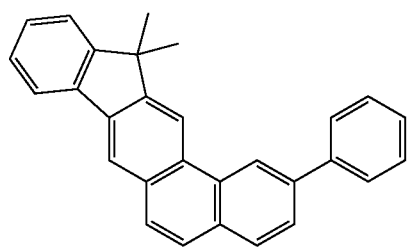

A102

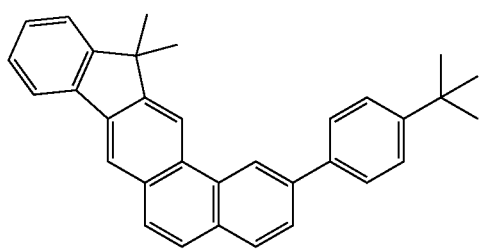

A103

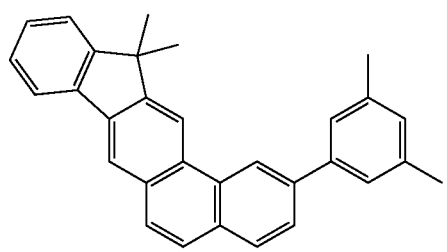

A104

-continued
A105
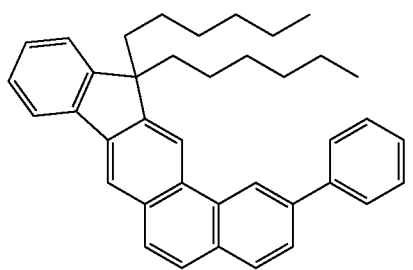
A106
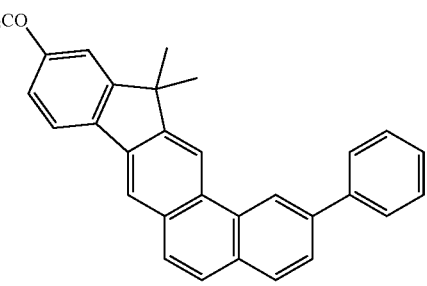
A107
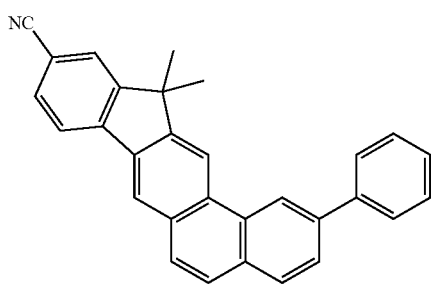
A108
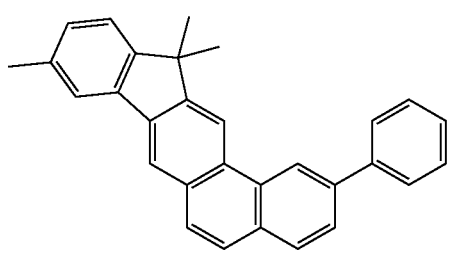
A109
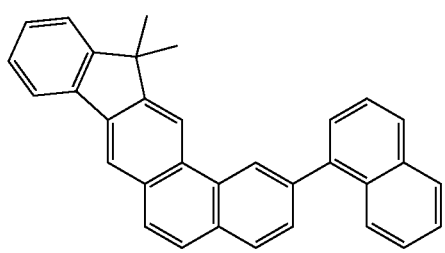
A110
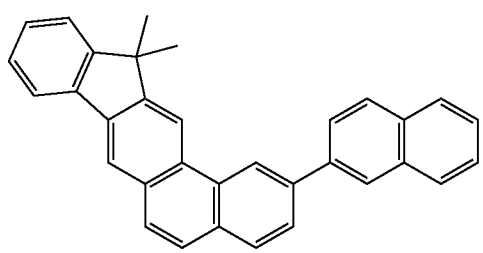
A111
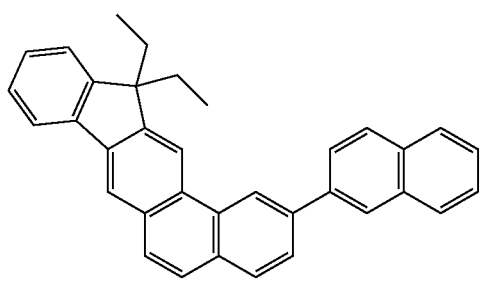
A112
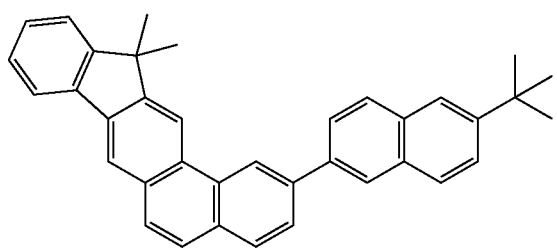
A113
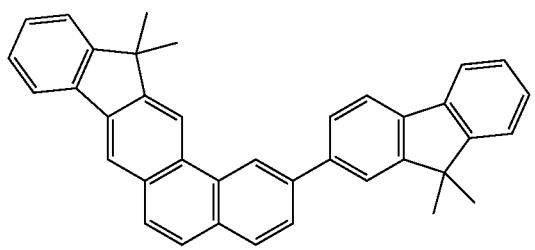
A114
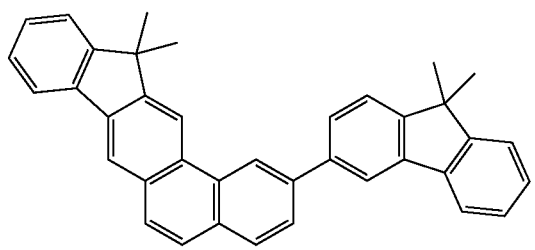

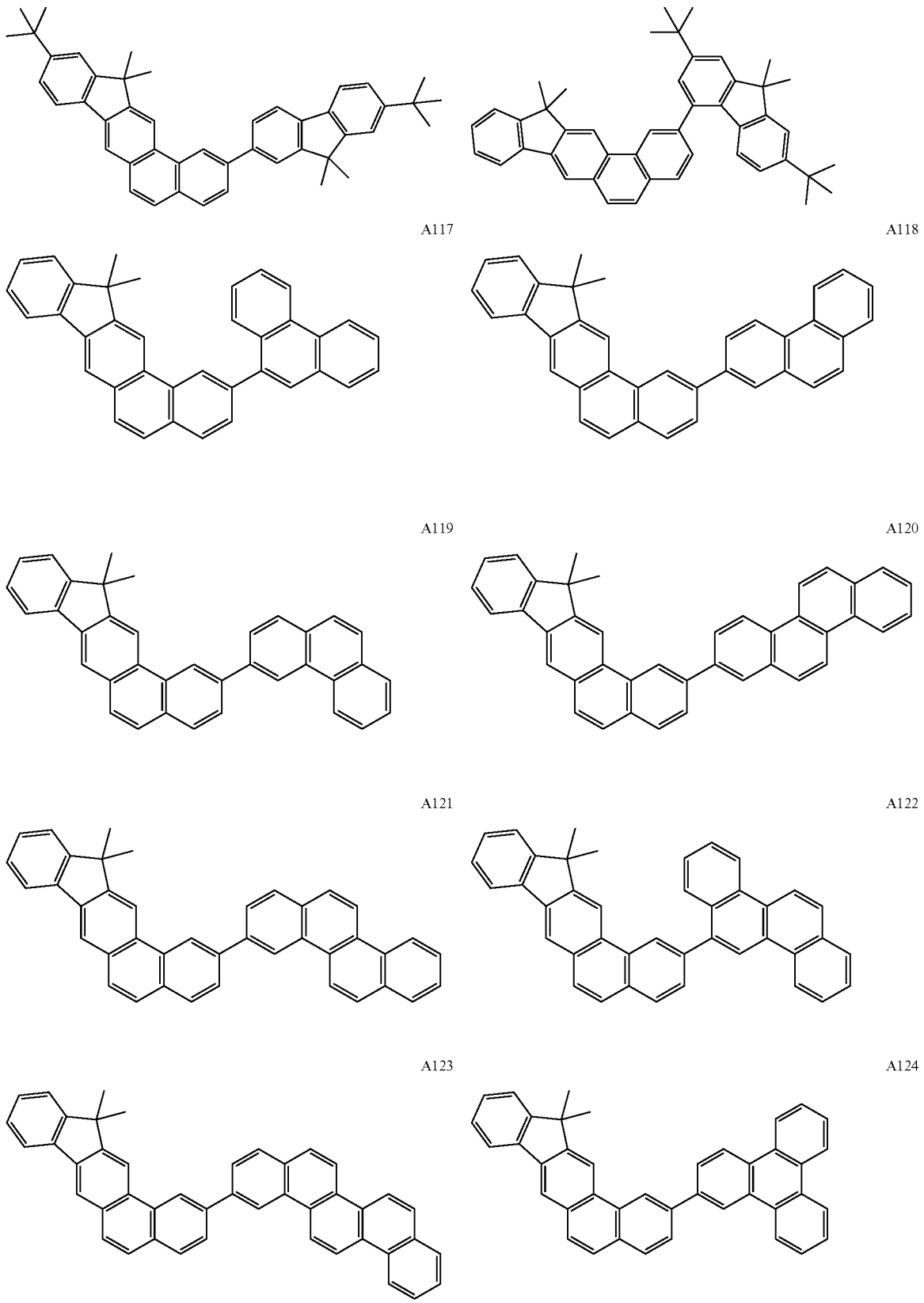

-continued
[Chem. 10]
A201
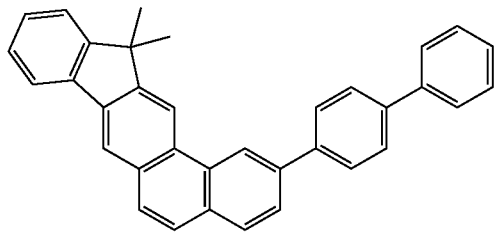
A202
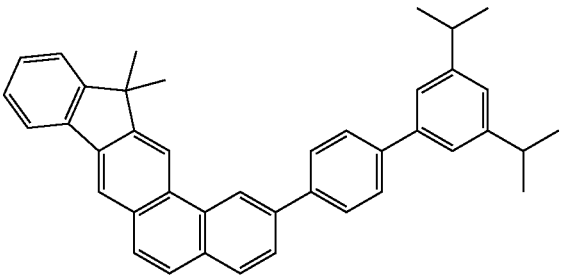
A203
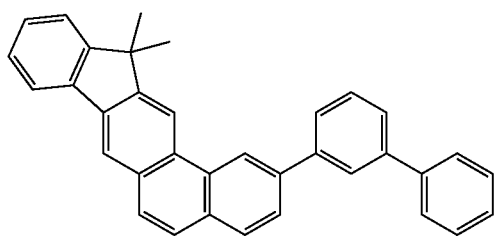
A204
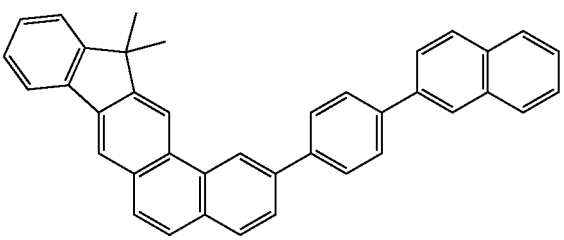
A205
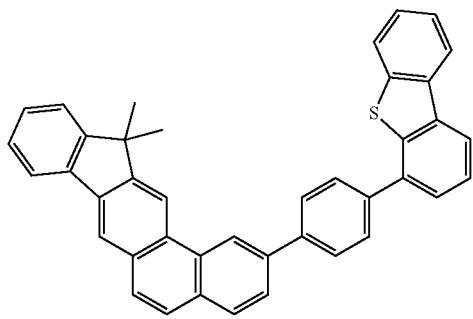
A206
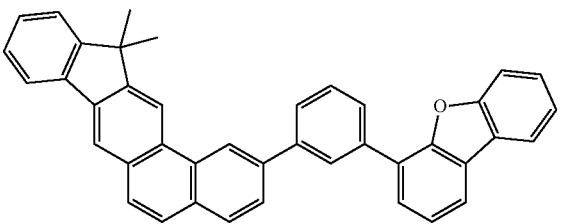
A207
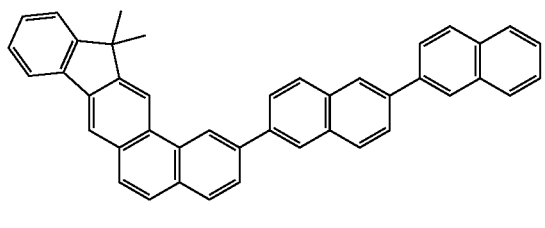
A208
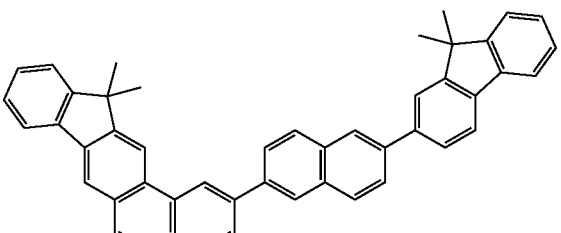
A209
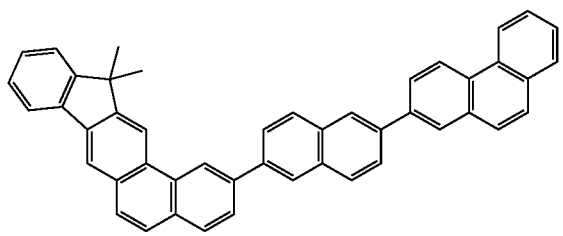
A210
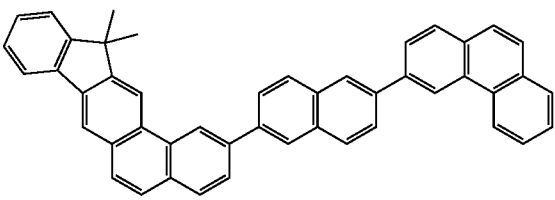

-continued
A211
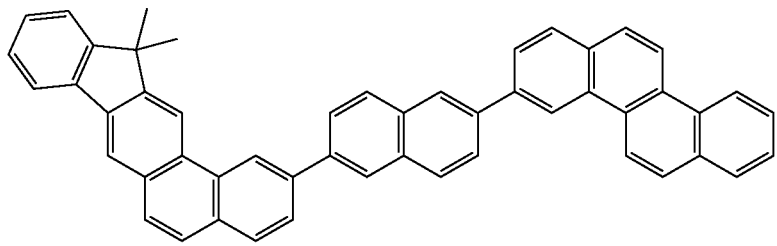
A212
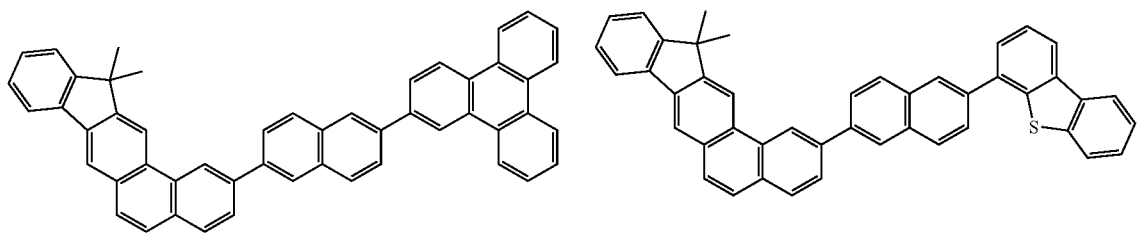
A213
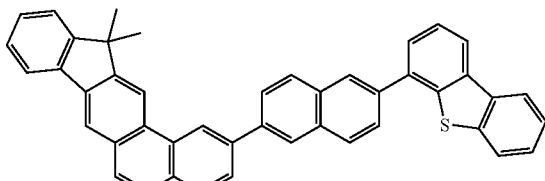
A214
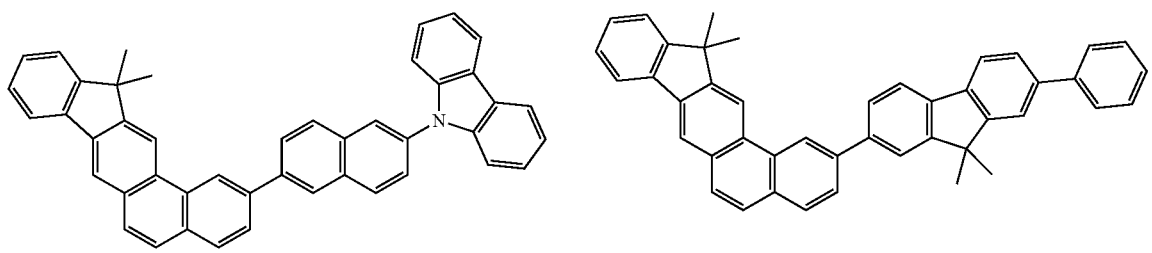
A215
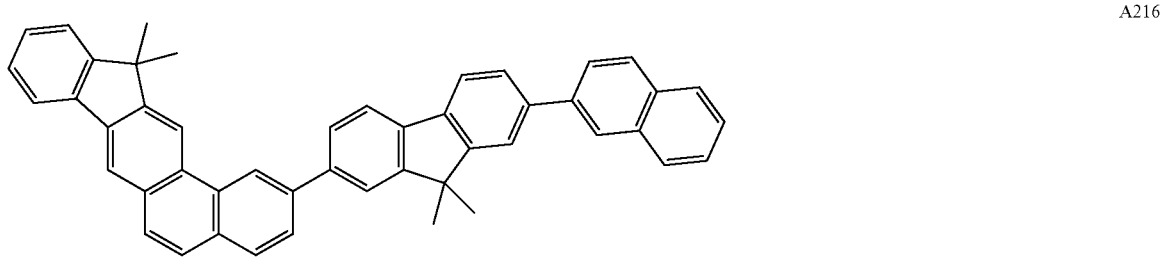
A216
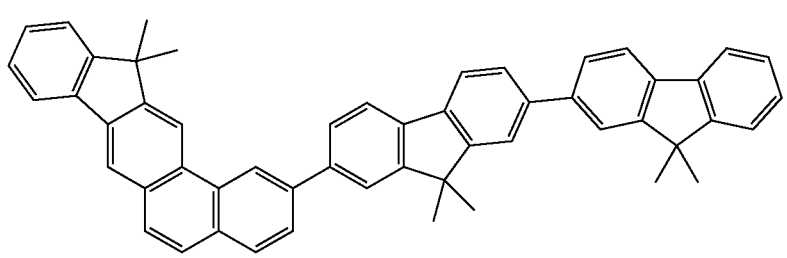
A217
A218
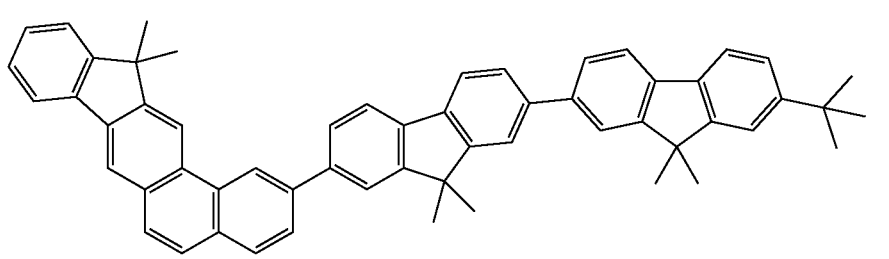

[Chem. 11]
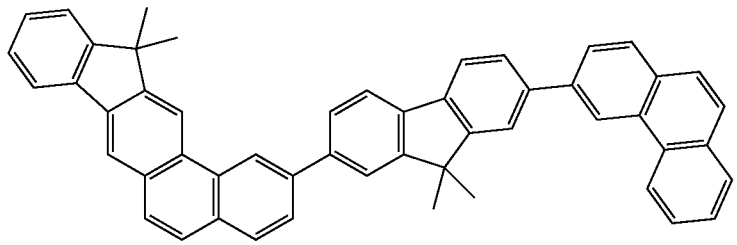
A219
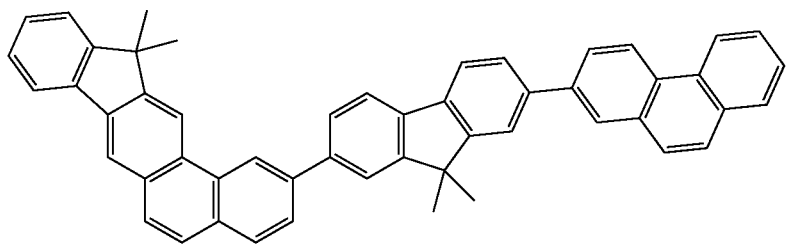
A220
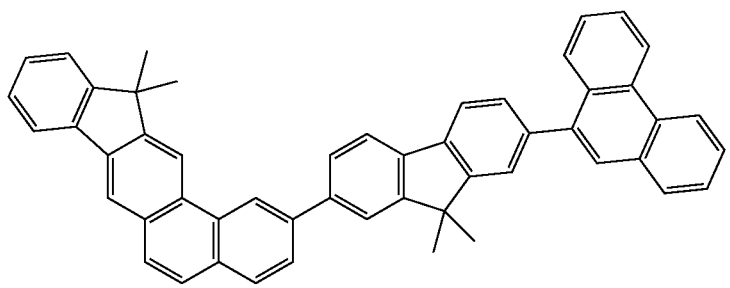
A221
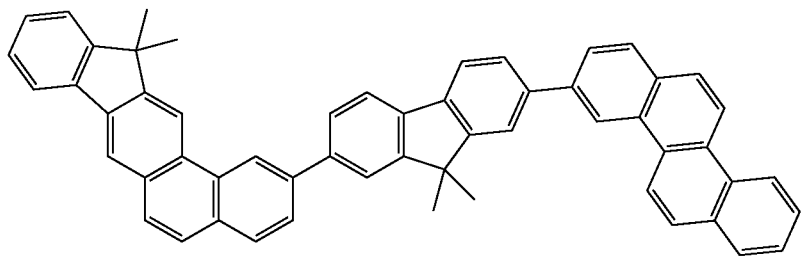
A222
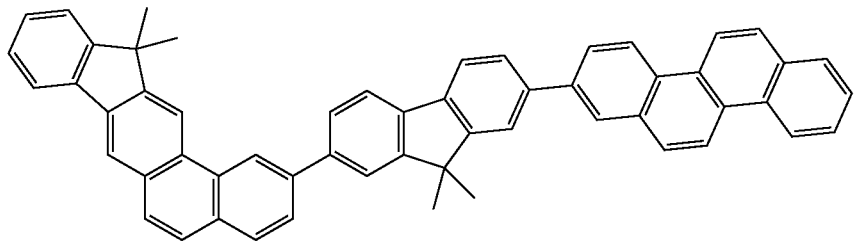
A223
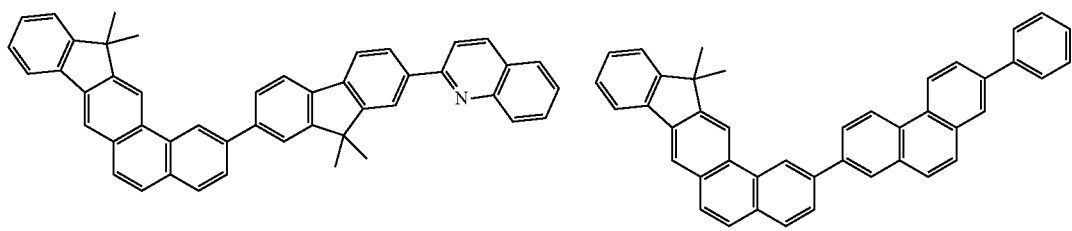
A224  A225

-continued
A226
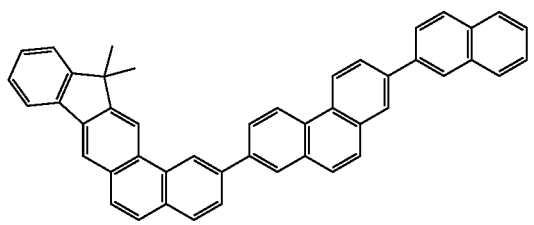
A227
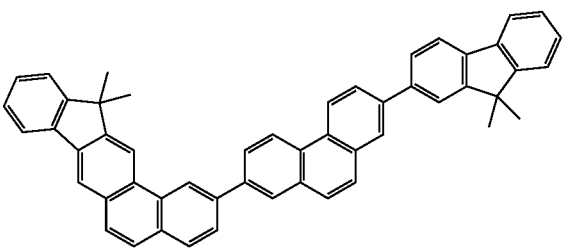
A228
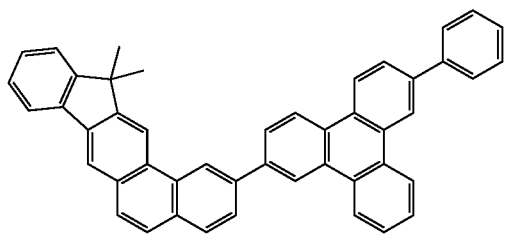
A229
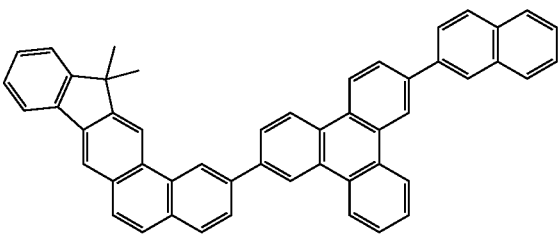
A230
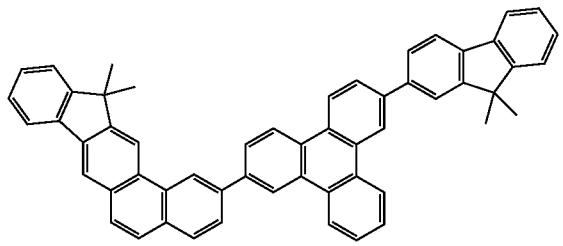
A231
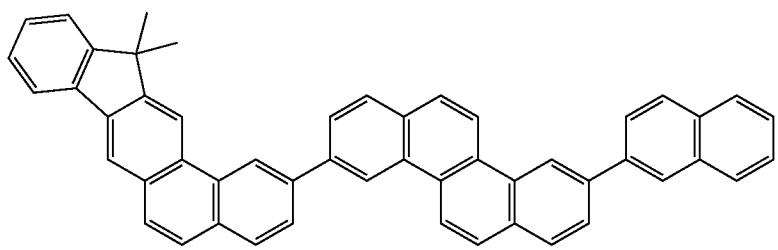
A232
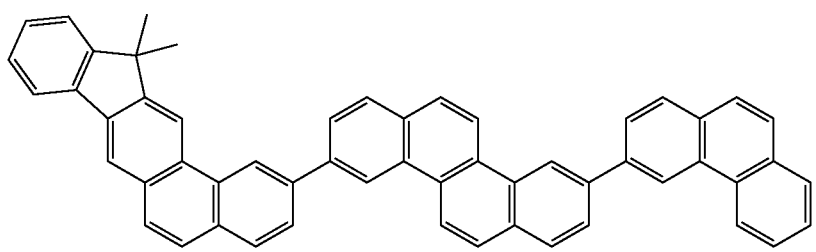
A233
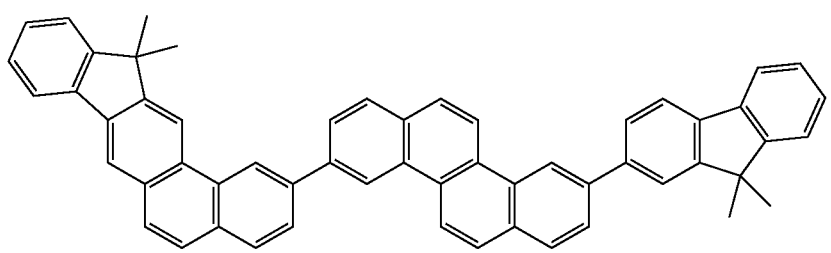
A234

[Chem. 12]
A301
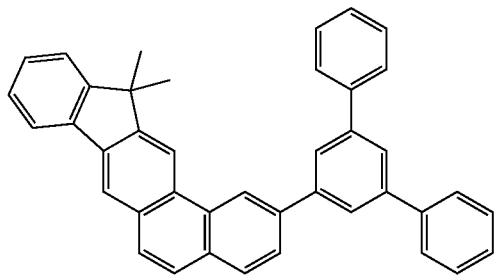
A302
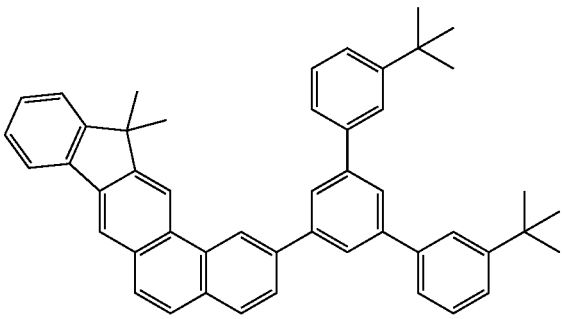
A303
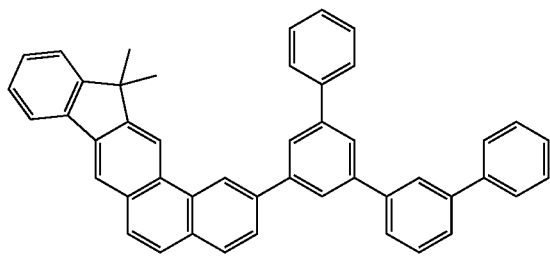
A304
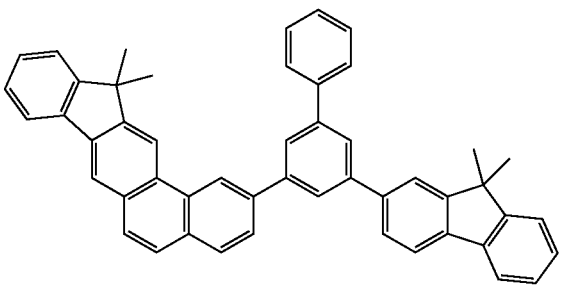
A305
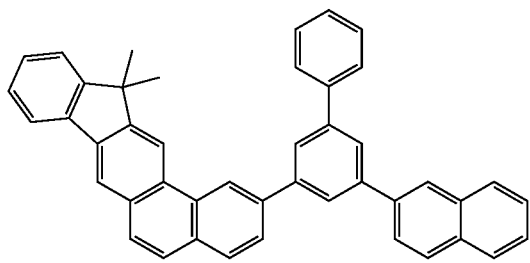
A306
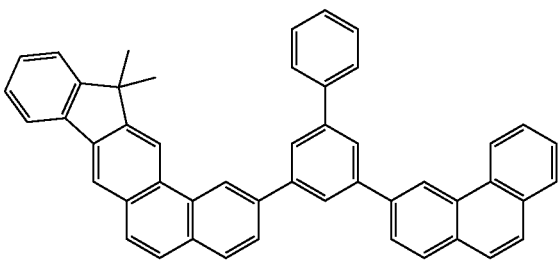
A307
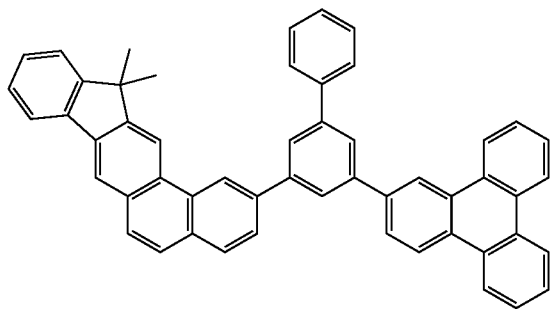
A308
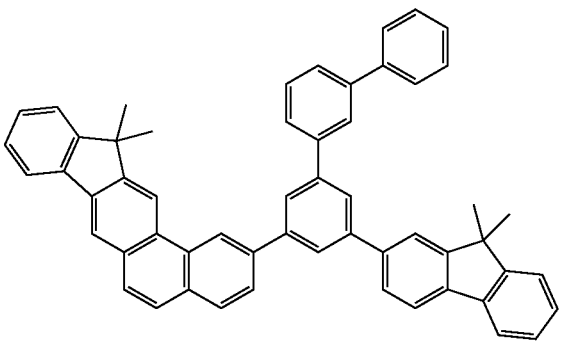

-continued
A309
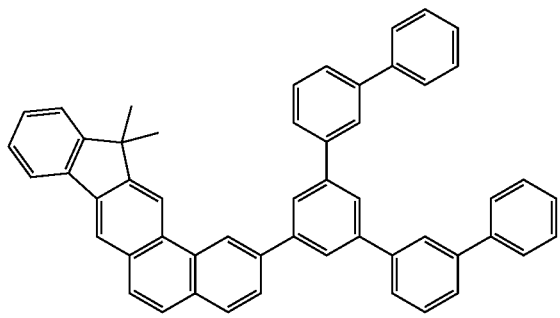
A310
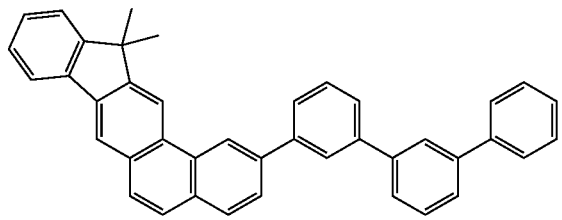
A311
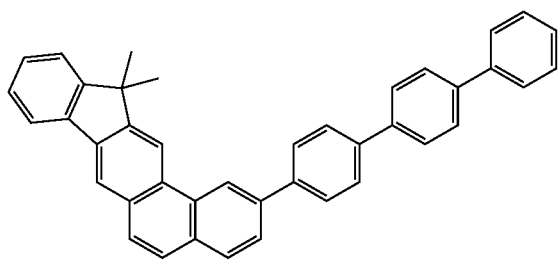
A312
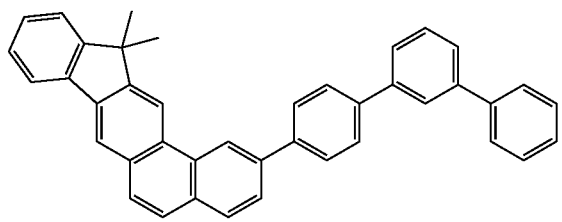
A313
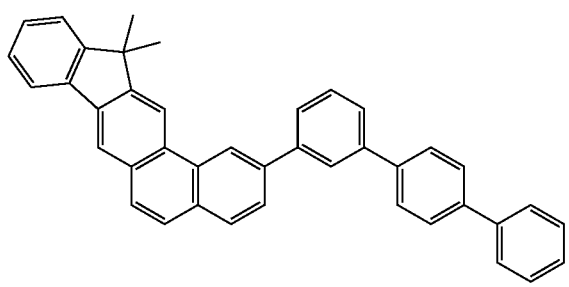
A314
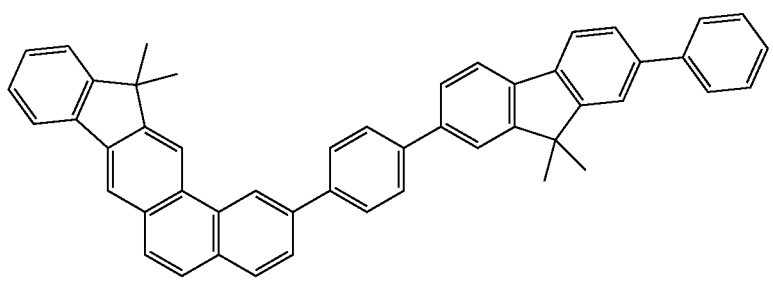
A315
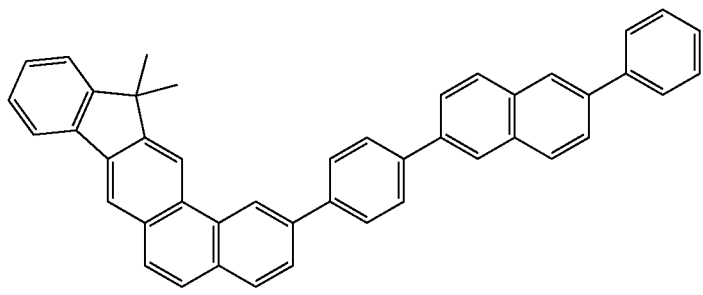

-continued
A316
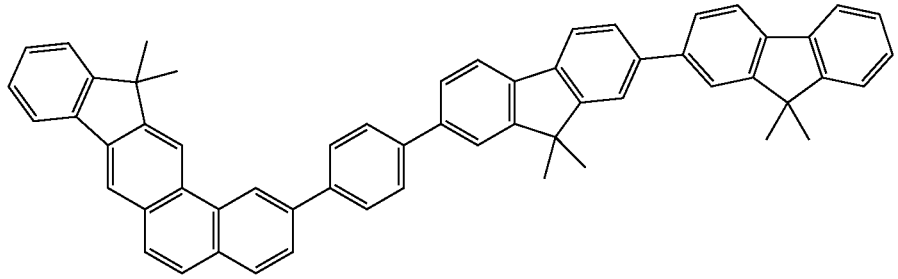
A317
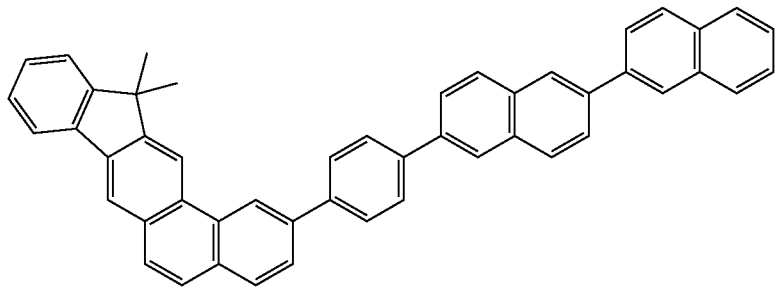
A318  A319
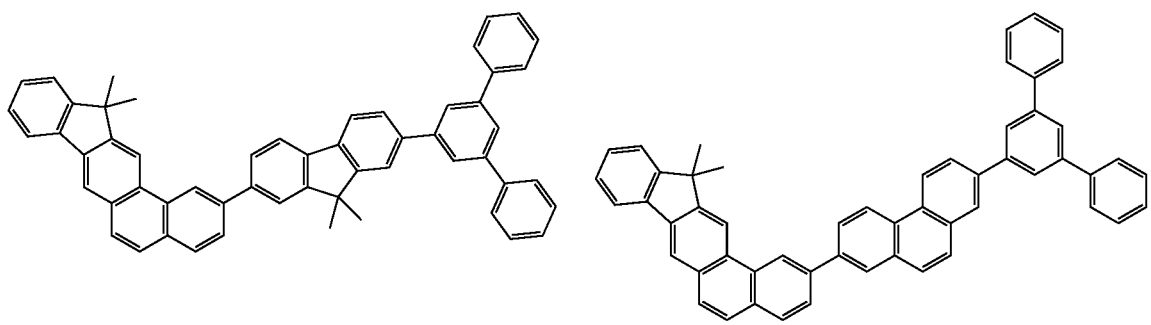
A320
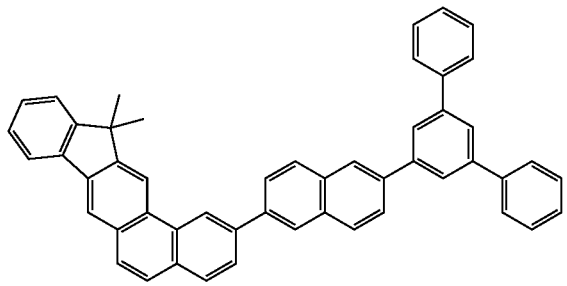
[Chem. 13]
A321
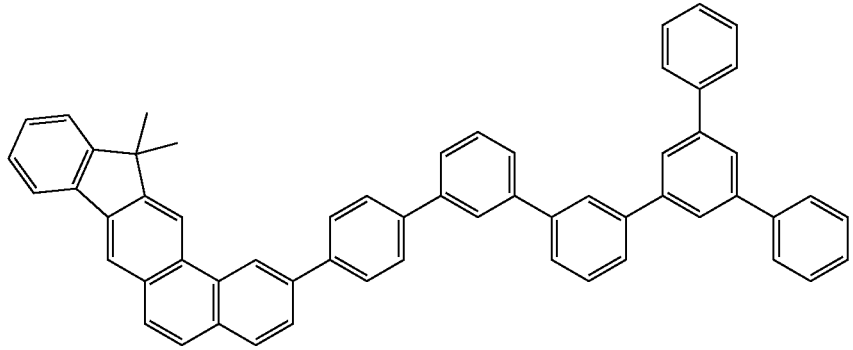

-continued
A322
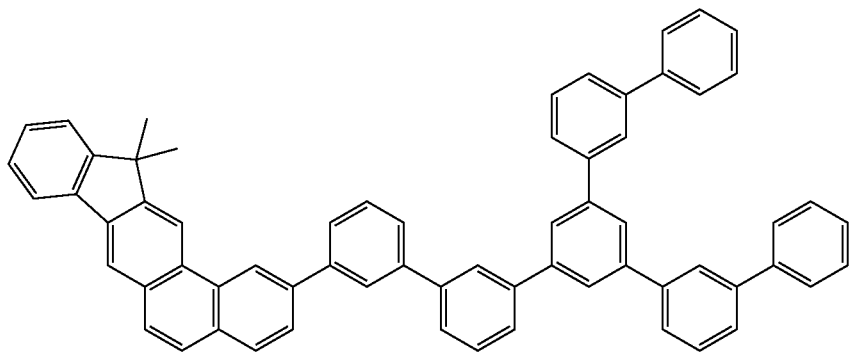
A323
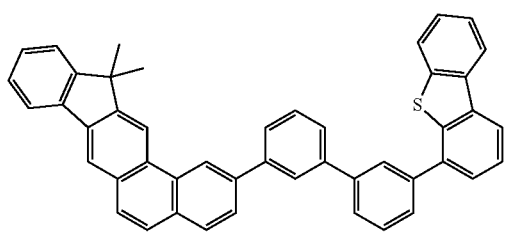
A324
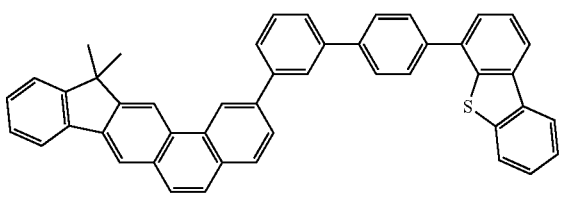
A325
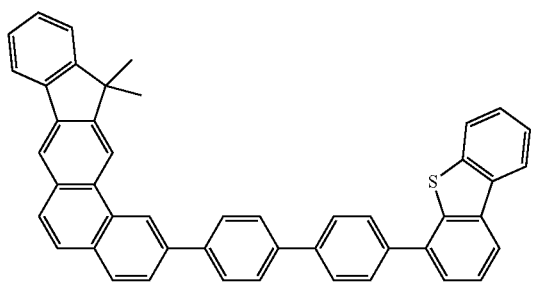
A326
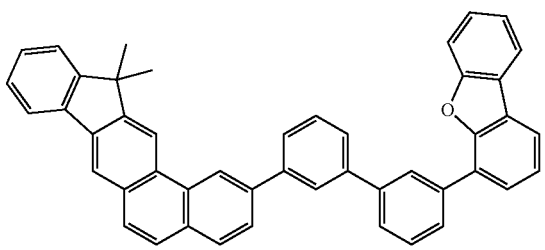
A327
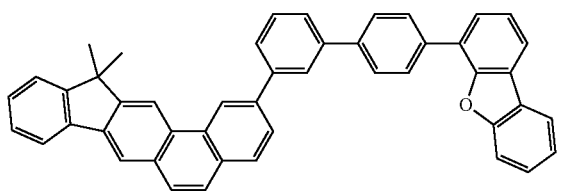
A328
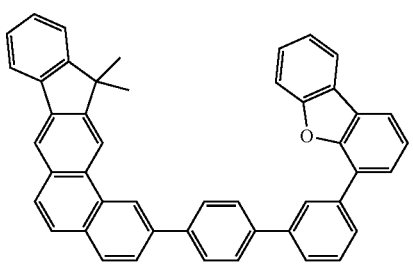
A329
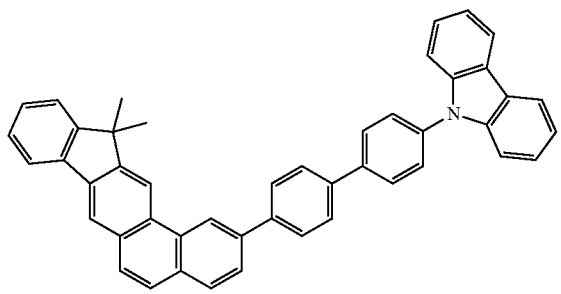
A330
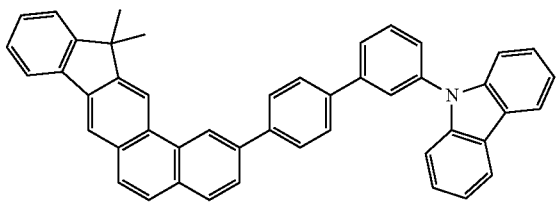

[Chem. 14]

A401
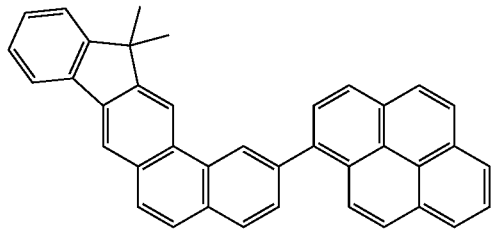

A402
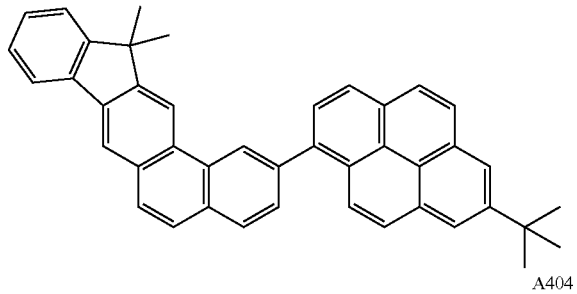

A403
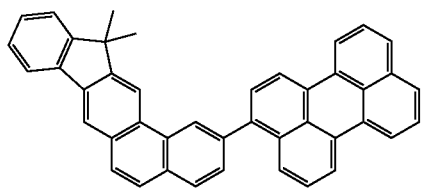

A404
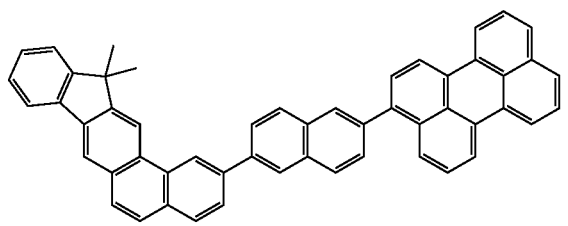

A405
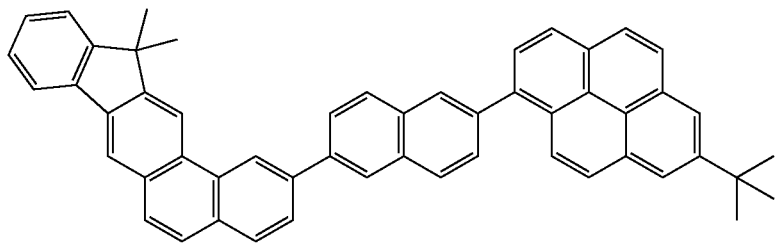

A406
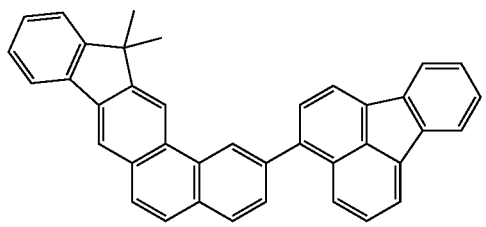

A407
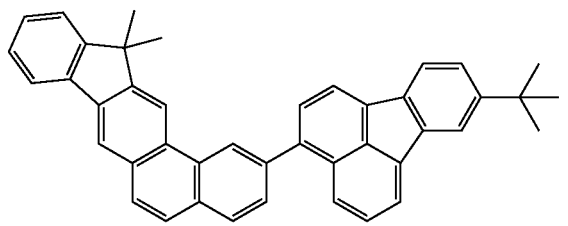

A408
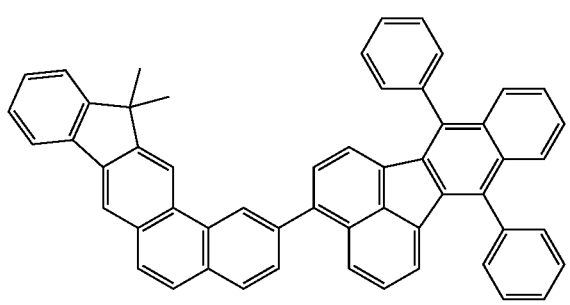

Among the example compounds shown above, example compounds A101 to A124 are each the indeno[1,2-b]phenanthrene compound represented by the general formula [1] and belong to a compound group in which n is 0. Since the compounds of a first group in which n is 0 each have a relatively high $S_1$ energy and a small molecular weight, the purification of the compound can be easily performed, for example, by sublimation purification. In addition, the compounds of the first group are each preferably used as the host for the red phosphorescent light emitting material.

Among the example compounds, example compounds A201 to A234 are each the indeno[1,2-b]phenanthrene compound represented by the general formula [2]. A second group compound corresponding to the compound represented by the formula [2] has a substituent formed of two aromatic rings connected to each other, and hence the π conjugation length of the whole compound, that is, the $S_1$ energy of the compound, is most preferable as the host for the red phosphorescent light emitting material.

Among the example compounds, example compounds A301 to A330 are each the indeno[1,2-b]phenanthrene compound represented by the general formula [1] in which a substituent formed of at least three aromatic rings is bonded to the indeno[1,2-b]phenanthrene skeleton. The compound of a third group having this structural characteristic is a compound in which in the general formula [1], n is at least 2, or n is 1 and one of the substituents $A_1$ and $A_2$ further has a phenyl group or a biphenyl group. In the example compounds, such as A301 to A310, A321, and A322, of the third group, the π conjugation is broken by the m-phenylene moiety included in the substituent. Hence, the HOMO of the compound itself is localized in the vicinity of the indeno[1,2-b]phenanthrene skeleton, and the π orbital do not extend onto the substituents corresponding to the substituents $A_1$ and $A_2$. Accordingly, in the compounds of the third group, besides the indeno moiety of the indeno[1,2-b]phenanthrene skeleton, the substituent bonded to this skeleton also functions as a HOMO sparse moiety, and hence, in particular, the hole mobility is characteristically low.

Among the indeno[1,2-b]phenanthrene compounds each represented by the general formula [1], example compounds A401 to A408 of the above example compounds are each the compound which includes as the substituent, an aromatic ring having $T_1$ energy lower than that of the indeno[1,2-b]phenanthrene skeleton. In compounds of a forth group corresponding to the above compounds, as in the compounds of the other groups, the hole mobility is also suppressed. In addition, since having a low $T_1$ energy, the compounds of the fourth group are each preferably used as the host for a fluorescent light emitting material.

Organic Light Emitting Element

Next, an organic light emitting element of the present invention will be described.

The organic light emitting element of the present invention at least includes two electrodes, that is, an anode and a cathode, facing each other and an organic compound layer disposed between the electrodes. In the organic light emitting element of the present invention, the organic compound layer at least includes a light emitting layer containing a light emitting material. In addition, the light emitting element of the present invention includes the indeno[1,2-b]phenanthrene compound of the present invention in the organic compound layer.

As an element structure of the organic light emitting element of the present invention, a multilayer element structure formed by sequentially laminating the following layers on a substrate may be mentioned.
(1) anode/light emitting layer/cathode
(2) anode/hole transport layer/light emitting layer/electron transport layer/cathode
(3) anode/hole transport layer/light emitting layer/electron transport layer/electron injection layer/cathode
(4) anode/hole injection layer/hole transport layer/light emitting layer/electron transport layer/cathode
(5) anode/hole injection layer/hole transport layer/light emitting layer/electron transport layer/electron injection layer/cathode
(6) anode/hole transport layer/electron blocking layer/light emitting layer/hole blocking layer/electron transport layer/cathode However, those element structure examples are merely basic element structures, and the structure of the organic light emitting element using the compound of the present invention is not limited to those mentioned above.

For example, the structure in which an insulating layer, an adhesive layer, or an interference layer is provided at the interface between the electrode and the organic compound layer may also be used. In addition, various structures, such as the structure in which the electron transport layer or the hole transport layer is formed of a plurality of layers having different ionization potentials and the structure in which the light emitting layer is formed of a plurality of layers containing different light emitting materials, may also be used.

In the present invention, for example, the above structure (6) in which the electron blocking layer and the hole blocking layer are both provided is preferably used. In the structure (6), since both carriers, holes and electrons, can be confined in the light emitting layer, no carrier leakage occurs, and hence a light emitting element having a high light emitting efficiency can be obtained.

The organic light emitting element of the present invention may be a bottom emission type in which light is extracted from an electrode located at a substrate side, a top emission type in which light is extracted from a side opposite to the substrate, or a type in which light is extracted from the top and the bottom surfaces.

The compound of the present invention is used mainly for the light emitting layer of the organic light emitting element. The light emitting layer in this case may be formed from one type component or may be formed from plural types of components. When the light emitting layer is formed from plural types of components, the components may be classified into a primary component and an accessory component.

The primary component is a compound having the highest weight ratio among all the compounds forming the light emitting layer and may be called a host. The accessory component is a compound other than the primary component and may be called a guest (dopant), a light emitting assistant material, or a charge injection material in accordance with the function and/or the role of the component.

In this embodiment, the guest is a compound primarily responsible for light emission in the light emitting layer. On the other hand, the host is a compound present in the light emitting layer as a matrix located around the guest and is a compound primarily responsible for transport of carriers and for supply of excitation energy to the guest.

The light emitting assist material is a compound which has a weight ratio smaller than that of the host in the light emitting layer, which is responsible to assist light emission of the guest, and which is also called a second host.

The concentration of the guest to the host is 0.01 to 50% by weight on the basis of the total amount of constituent materials of the light emitting layer and preferably 0.1 to 20% by weight. In addition, in order to prevent concentration quenching, the concentration of the guest is particularly preferably 0.1 to 10% by weight.

In addition, the guest may be uniformly contained in the whole layer formed of the host, may be contained therein so as to have a predetermined concentration gradient, or may be contained partially in a specific region so as to form a region which is only composed of the host without the guest.

As described above, although being preferably used as the host of the light emitting layer, the indeno[1,2-b]phenanthrene compound of the present invention is more preferably used as the host of the light emitting layer for the guest formed of a phosphorescent light emitting material. That is, the indeno[1,2-b]phenanthrene compound of the present invention is preferably used as the host in the light emitting layer of a phosphorescent light emitting element.

As the phosphorescent light emitting material used as the guest of the light emitting layer, for example, metal complexes, such as an iridium complex, a platinum complex, a rhenium complex, a copper complex, a europium complex, and ruthenium complex, may be mentioned. Among those mentioned above, an iridium complex having intensive phosphorescent light emitting ability is preferable. In this case, the light emitting color of the phosphorescent light emitting material has a maximum light emission peak wavelength of 580 to 630 nm in relationship with the $T_1$ energy described above. In addition, in order to assist the transmittance of excitons and/or electrons, one light emitting layer may contain a plurality of phosphorescent light emitting materials.

The organic light emitting element of the present invention may be a light emitting element which emits white light. In this case, the light emitting layer has a plurality of light emitting materials, and at least one of the above materials is the indeno[1,2-b]phenanthrene compound of the present invention.

Hereinafter, although specific examples of the iridium complex used as the phosphorescent light emitting material contained in the organic light emitting element of the present invention will be shown below, the present invention is not limited thereto.

[Chem. 15]

Ir-1

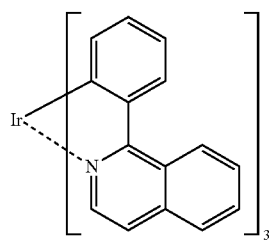

Ir-2

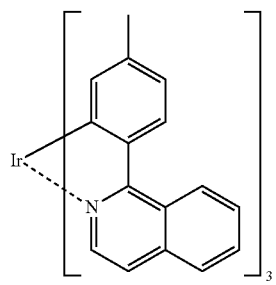

Ir-3

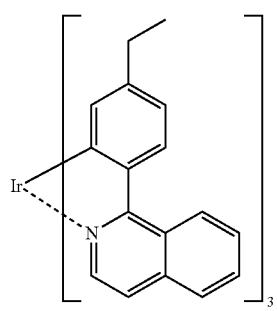

Ir-4

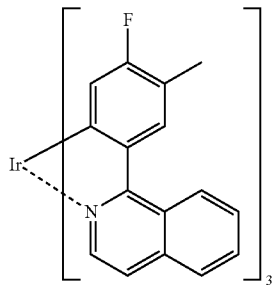

Ir-5

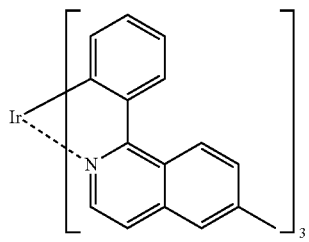

Ir-6

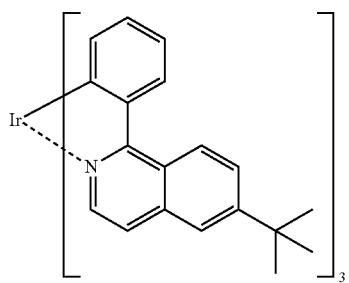

Ir-7

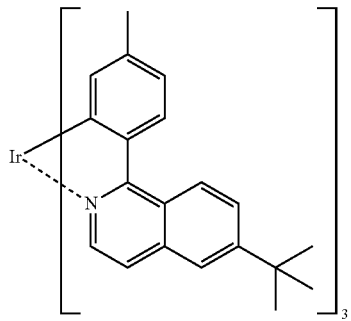

Ir-8

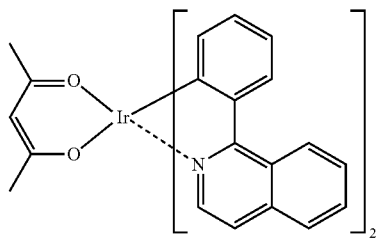

Ir-9

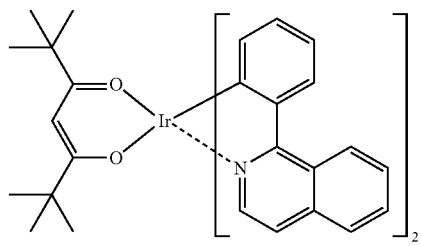

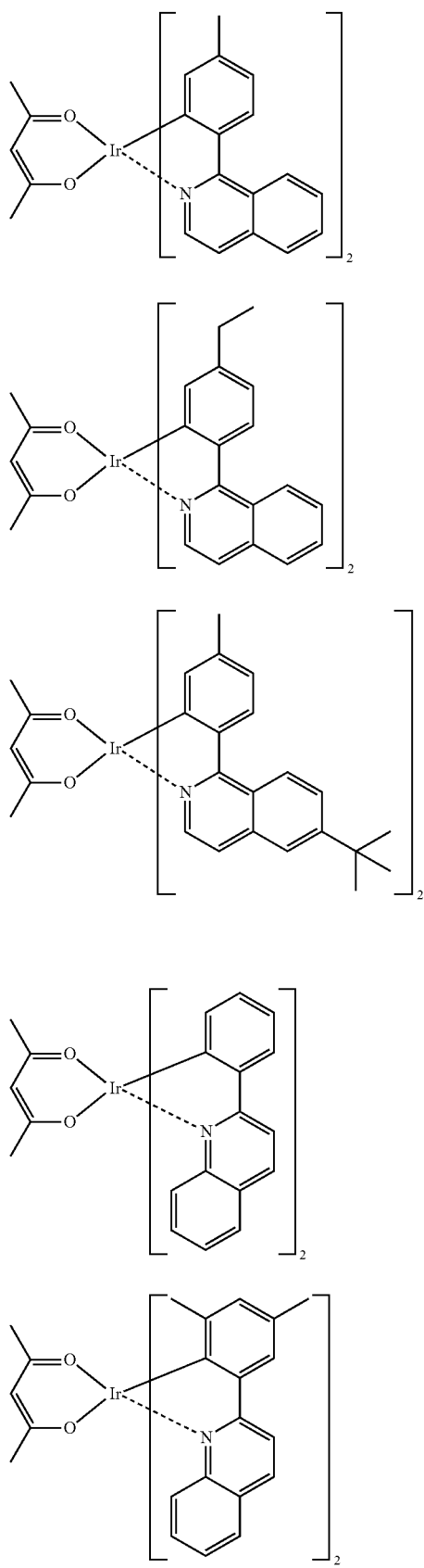

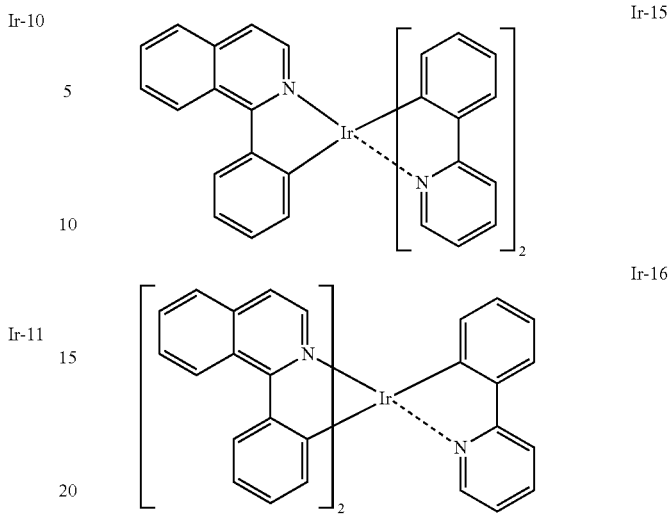

In the organic light emitting element of the present invention, besides the indeno[1,2-b]phenanthrene compound of the present invention, if necessary, known low molecular weight and high molecular weight materials may also be used. In more particular, a hole injection/transport material, a host, a light emitting material, an electron injection/transport material, and the like may also be used in combination.

Hereinafter, specific examples of those materials will be described below.

As the hole injection/transport material, a material having high hole mobility is preferable so that holes from the anode are easily injected, and injected holes can be transported to the light emitting layer. In addition, in order to prevent degradation in film quality, such as crystallization, in the element, a material having a high glass transition temperature is preferable. As the low molecular weight and the high molecular weight material having hole injection/transport ability, for example, there may be mentioned a triarylamine derivative, an arylcarbazole derivative, a phenylenediamine derivative, a stilbene derivative, a phthalocyanine derivative, a porphyrin derivative, a poly(vinyl carbazole), a poly(thiophene), and other electrical conductive polymers.

As the light emitting material primarily responsible for light emitting function, besides the above phosphorescent light emitting guest materials or derivatives thereof, for example, there may be mentioned fused ring compounds (including a fluorene derivative, a naphthalene derivative, a pyrene derivative, a perylene derivative, a tetracene derivative, an anthracene derivative, and rubrene), quinacridone derivatives, coumarin derivatives, stilbene derivatives, organic aluminum complexes, such as tris(8-quinolinolato) aluminum, organic beryllium complexes, poly(phenylene vinylene) derivatives, polyfluorene derivatives, and polyphenylene derivatives.

As the host material of the light emitting layer, besides the indeno[1,2-b]phenanthrene compound of the present invention, aromatic hydrocarbon compounds and derivatives thereof may be mentioned, and in addition, for example, carbazole derivatives, dibenzofuran derivatives, dibenzothiophene derivatives, organic aluminum complexes, such as tris(8-quinolinolate)aluminum, and organic beryllium complexes may also be mentioned.

As the electron injection/transport material, in consideration of the balance with the hole mobility of the hole transport material, a material may be arbitrarily selected from materials into which electrons from the cathode are easily injected and which can transport injected electrons to the light emitting layer. As a material having electron injection ability and electron transport ability, for example, there may be mentioned oxadiazole derivatives, oxazole derivatives, pyrazine derivatives, triazole derivatives, triazine derivatives, quinoline derivatives, quinoxaline derivatives, phenanthroline derivatives, and organic aluminum complexes.

As a constituent material of the anode, a material having a work function as large as possible is preferable. For example, there may be used metal elements, such as gold, platinum, silver, copper, nickel, palladium, cobalt, selenium, vanadium, and tungsten; an alloy using the metal elements mentioned above in combination; and metal oxides, such as tin oxide, zinc oxide, indium oxide, indium tin oxide (ITO), and indium zinc oxide. In addition, electrical conductive polymers, such as a polyaniline, a polypyrrole, and a polythiophene, may also be used.

Those electrode materials may be used alone, or at least two thereof may be used in combination. In addition, the anode may be formed from either one layer or a plurality of layers.

On the other hand, as a constituent material of the cathode, a material having a work function as small as possible is preferable. For example, there may be mentioned alkali metals, such as lithium; alkali earth metals, such as calcium; and metal elements, such as aluminum, titanium, manganese, silver, lead, and chromium. In addition, alloys formed in combination of the above metal elements may also be used. For example, magnesium-silver, aluminum-lithium, and aluminum-magnesium may be used. Metal oxides, such as indium tin oxide (ITO), may also be used.

Those electrode materials may be used alone, or at least two thereof may be used in combination. In addition, the cathode may be formed from either one layer or a plurality of layers.

In the organic light emitting element of the present invention, a layer containing the organic compound of the present invention and a layer formed from another organic compound may be formed by the following method.

The organic compound layer forming the organic light emitting element of the present invention may be formed by a vacuum deposition method, an ionization deposition method, a sputtering method, a plasma deposition method, or a known coating method (such as a spin coating method, a dipping method, a casting method, an LB method, or an ink jet method) in which the organic compound is dissolved in an appropriate solvent.

When the layer is formed by a vacuum deposition method or a solution coating method, crystallization and the like are not likely to occur, and excellent aging stability can be obtained. In addition, when the film is formed by a coating method, the film may also be formed in combination with an appropriate binder resin.

As the binder resin described above, although a poly(vinyl carbazole) resin, a polycarbonate resin, a polyester resin, an ABS resin, an acrylic resin, a polyimide resin, a phenol resin, an epoxy resin, a silicone resin, a urea resin, and the like may be mentioned by way of example, the binder resin is not limited to those mentioned above.

In addition, those binder resins may be used alone as a homopolymer or a copolymer, or at least two types thereof may be used in combination. Furthermore, if necessary, additives, such as known plasticizer, antioxidant, and UV absorber, may also be used in combination.

Application of Organic Light Emitting Element

The organic light emitting element of the present invention may be used as a constituent member of a display device or a lighting device. In addition, the organic light emitting element of the present invention may also be used, for example, as an exposure light source of an electrophotographic image forming device, a backlight of a liquid crystal display device, and lighting. In addition, the organic light emitting element may further include a color filter.

A display device of the present invention has a display unit including a plurality of pixels each having the organic light emitting element of the present invention.

In addition, this pixel includes the organic light emitting element of the present invention and an active element. As one example of the active element, a switching element controlling the light emitting luminance may be mentioned, and as one example of the switching element, a TFT element may be mentioned.

The anode or the cathode of the organic light emitting element included in the pixel is connected to a drain electrode or a source electrode of the TFT element. In addition, the display device may be used as an image display device of a personal computer (PC). In addition, the TFT element is provided on an insulating surface of the substrate.

The display device may be an image information processing device which has an input unit inputting image information from an area CCD, a linear CCD, or a memory card and which displays an inputted image on a display unit.

In addition, the display unit of the image information processing device or the image forming device may have a touch panel function. In addition, the display device may be used as a display unit of a multifunctional printer.

The lighting device is a device that lights a room. The lighting device may be a device emitting light color selected from white, neutral white, and others including blue to red.

The lighting device of the present invention has the organic light emitting element of the present invention and an AC/DC converter circuit connected thereto. In addition, the lighting device may further include a color filter.

The AC/DC converter circuit forming the lighting device of the present invention is a circuit which converts an alternating-current voltage to a direct-current voltage.

The image forming device of the present invention is an image forming device having a photosensitive body, a charging unit charging a surface of this photosensitive body, an exposing unit exposing the photosensitive body to form an electrostatic latent image, and a developer developing the electrostatic latent image formed on the surface of the photosensitive body. The exposing unit of this image forming device includes the organic light emitting element of the present invention.

Figure 2:
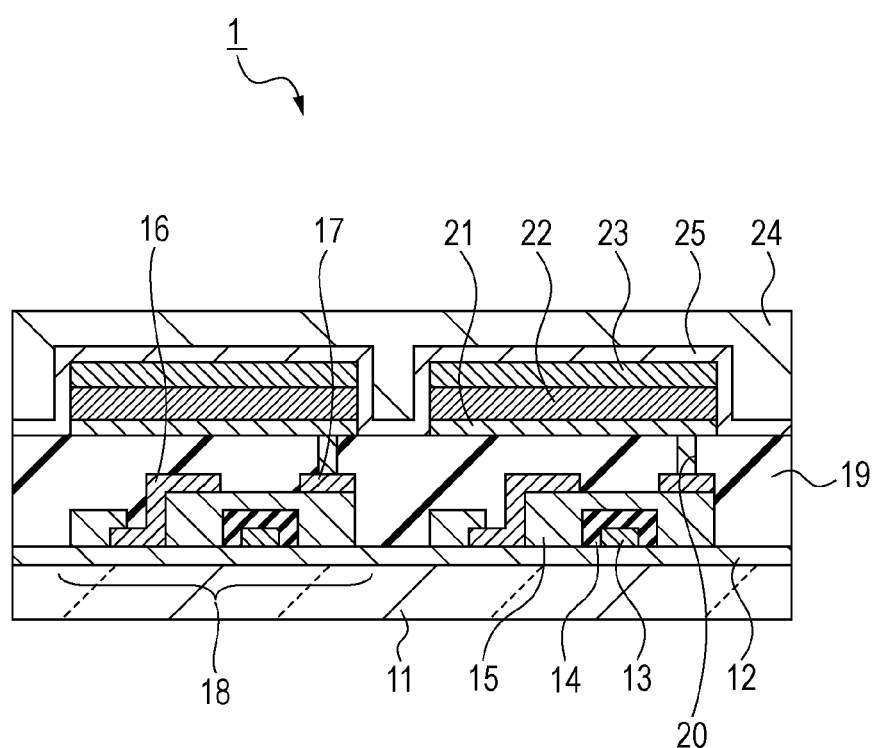
FIG. 2 is a schematic cross-sectional view showing an organic light emitting element and a switching element connected thereto.

Next, with reference to the drawing, the display device of the present invention will be described. FIG. 2 is a schematic cross-sectional view showing one example of a display device having an organic light emitting element and a TFT element connected thereto. In addition, as the organic light emitting element forming a display device 1 shown in FIG. 2, the organic light emitting element of the present invention is used.

The display device 1 shown in FIG. 2 includes a substrate 11 formed, for example, of glass and a damp-proof film 12 provided thereon to protect the TFT element or an organic compound layer. In addition, reference numeral 13 indicates a gate electrode. Reference numeral 14 indicates a gate insulating film, and reference numeral 15 indicates a semiconductor layer.

A TFT element 18 has the semiconductor layer 15, a drain electrode 16, and a source electrode 17. On the TFT element 18, an insulating film 19 is provided. An anode 21 forming the organic light emitting element is connected to the source electrode 17 via a contact hole 20.

In addition, an electrode connection method between the electrode (anode or cathode) included in the organic light emitting element and the electrode (source electrode or drain electrode) included in the TFT is not limited to the mode shown in FIG. 2. That is, one of the anode and the cathode may be electrically connected to one of the source electrode and the drain electrode of the TFT element.

In the display device 1 shown in FIG. 2, although organic compound layers are shown as if formed from one layer, an organic compound layer 22 may include a plurality of layers. On a cathode 23, a first protective layer 24 and a second protective layer 25 are provided so as to suppress degradation of the organic light emitting element.

When the display device 1 shown in FIG. 2 is a display device emitting white light, a light emitting layer included in the organic compound layer 22 in FIG. 2 may be a layer formed by mixing a red light emitting material, a green light emitting material, and a blue light emitting material. In addition, there may also be used a laminate type light emitting layer formed by laminating a layer formed from a red light emitting material, a layer formed from a green light emitting material, and a layer formed from a blue light emitting material. Furthermore, as another method, a layer formed from a red light emitting material, a layer formed from a green light emitting material, and a layer formed from a blue light emitting material may be arranged side by side to form domains in one light emitting layer.

In the display device 1 shown in FIG. 2, although a transistor is used as the switching element, instead of the transistor, an MIM element may also be used as the switching element.

In addition, the transistor used in the display device 1 shown in FIG. 2 is not limited to a transistor formed from a single crystal silicon wafer and may be a thin film transistor having an active layer on an insulating surface of the substrate. For example, there may also be used a thin film transistor using single crystal silicon as the active layer, a thin film transistor using non-single crystal silicon, such as amorphous silicon or fine crystalline silicon, as the active layer, and a thin film transistor using non-single crystal oxide semiconductor, such as a indium zinc oxide or an indium gallium zinc oxide, as the active layer. Incidentally, the thin film transistor may also be called a TFT element.

The transistor included in the display device 1 shown in FIG. 2 may be formed in the substrate, such as a Si substrate. In this embodiment, "the transistor is formed in the substrate" means that the substrate, such as a Si substrate, itself is processed to form a transistor. That is, "the transistor is provided in the substrate" may also mean that the substrate and the transistor are integrally formed.

Whether the transistor is formed in the substrate or not may be determined depending on the definition. For example, when the definition per inch is approximately equal to that of QVGA, the organic light emitting element is preferably provided in a Si substrate.

As thus has been described, when a display device using the organic light emitting element of the present invention is driven, a preferable image quality can be obtained, and stable display can also be obtained even if display is performed for a long time.

In addition, the indeno[1,2-b]phenanthrene compound of the present invention may be used not only for an organic light emitting element but may also be used as a constituent material of a biological marker or a filter film.

EXAMPLES

Example 1

Synthesis of Example Compound A211

(1) Synthesis of InPtCl-1

[Chem. 16]

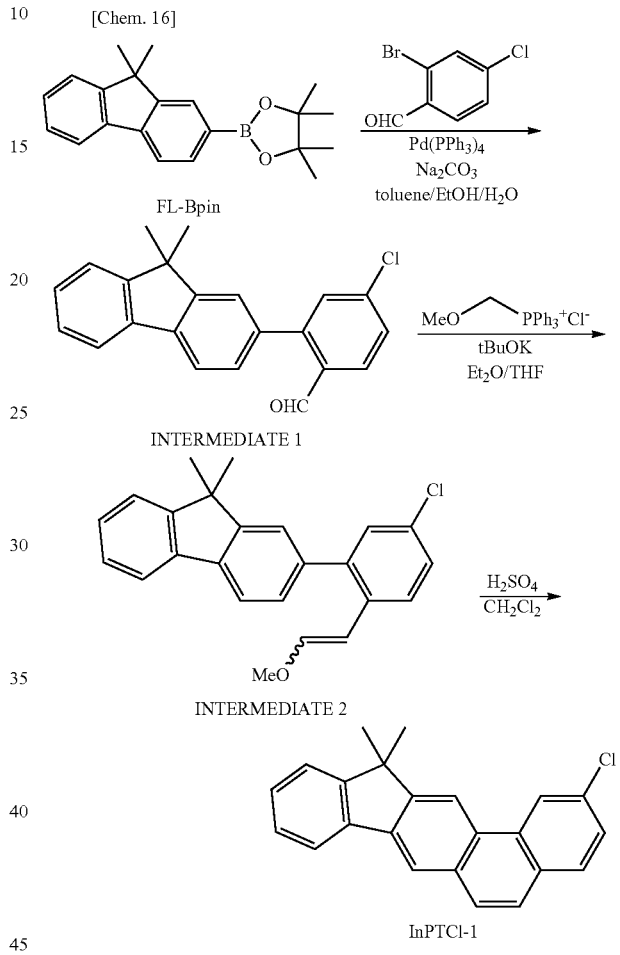

The following reagents and solvents were charged into a 200-ml recovery flask.
2-bromo-4-chlorobenzaldehyde: 3.00 g (13.7 mmol)
FL-Bpin: 4.47 g (13.9 mmol)
Tetrakis(triphenylphosphine)palladium(0): 474 mg (0.41 mmol)
Toluene: 60 mL
Ethanol: 30 mL
10-wt % aqueous sodium carbonate solution: 30 mL Next, the reaction solution was refluxed by heating for 2 hours with stirring under nitrogen. After the reaction was completed, to the reaction solution was added toluene and water and the mixture was stirred, and an organic layer was then separated by a liquid separation operation. Subsequently, after being washed with a saturated aqueous sodium chloride solution, the organic layer was dried over sodium sulfate. The organic layer was then concentrated under reduced pressure, so that a crude product was obtained. This crude product was then purified by a silica gel column chromatography (eluent: heptane/chloroform=2/1), so that 4.33 g (yield: 95%) of the intermediate 1 was obtained.

Next, 9.37 g (27.3 mmol) of (methoxymethyl)triphenylphosphonium chloride and 50 mL of dehydrated diethyl ether were charged into a nitrogen-replaced 500-mL recovery flask at room temperature. Subsequently, while the reaction solution was stirred, 27.3 mL (27.3 mmol) of a 1M THF solution of tert-butoxy potassium was added thereto, and stirring was further performed for 1 hour. A solution in which 4.33 g (13.0 mmol) of the above intermediate 1 was dissolved in 90 mL of a THF solvent was then added to the reaction solution. After the reaction solution was then further stirred for 3 hours at room temperature, water was added thereto so as to quench the reaction. Next, after a water layer was extracted three times with ethyl acetate by a liquid separation operation, the collected organic layer was washed with a saturated aqueous sodium chloride solution and was then dried over sodium sulfate. Subsequently, the organic layer was concentrated under reduced pressure, so that a crude product was obtained. This crude product was then purified by a silica gel column chromatography (eluent: heptane/chloroform=2/1), so that 4.50 g (yield: 96%) of the intermediate 2 was obtained.

Next, after 180 mL of dehydrated dichloromethane and 2.0 mL of concentrated sulfuric acid were charged into a nitrogen-replaced 500-mL recovery flask and were sufficiently stirred, a solution in which 4.50 g (12.5 mmol) of the intermediate 2 was dissolved in 20 mL of a dichloromethane solvent was added dropwise to the reaction solution at room temperature. Subsequently, after the reaction solution was further stirred at room temperature for 30 minutes, water was added thereto so as to quench the reaction. Next, after the reaction solution was neutralized, and a water layer was then extracted once with chloroform by a liquid separation operation, the collected organic layer was washed with a saturated aqueous sodium chloride solution and was then dried over magnesium sulfate. Subsequently, the organic layer was concentrated under reduced pressure, so that a crude product was obtained. This crude product was then purified by a silica gel column chromatography (eluent: heptane/chloroform=5/1), so that 3.83 g (yield: 93%) of InPTCl-1 was obtained.

InPTCl-1 thus obtained was identified by the following method.

MALDI-TOF-MS (Matrix-Assisted Laser Desorption-Ionization Mass Spectrometry)

Observed value: m/z=328.102, calculated value: $C_{23}H_{17}Cl$=328.288

[$^1$H-NMR (400 MHz, CDCl$_3$)]

δ 8.71(d,1H), 8.61(s,1H), 8.19(s,1H), 7.91-7.88(dd,1H), 7.82(d,2H), 7.68(d,1H), 7.55-7.50(m,2H), 7.42-7.39(m,2H), 1.66(s,6H).

(2) Synthesis of InPTBpin-1

[Chem. 17]

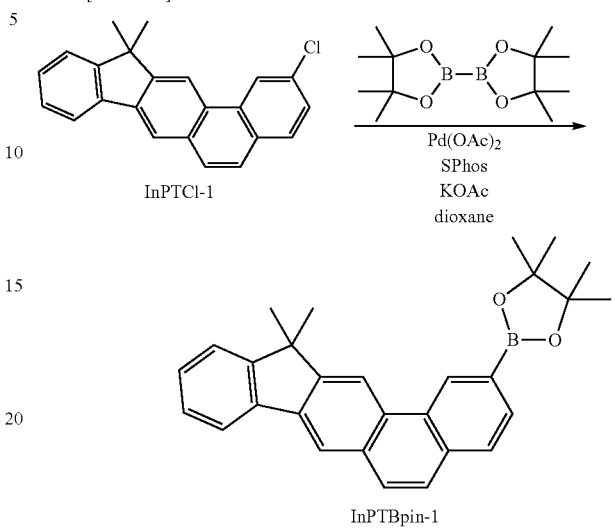

The following reagents and solvents were charged into a nitrogen-replaced 100-ml recovery flask.

InPTCl-1: 1.20 g (3.65 mmol)
Bis(pinacolato)diboron: 1.11 g (4.38 mmol)
Palladium(0) acetate: 41 mg (0.182 mmol)
SPhos (2-dicyclohexylphosphino-2',6'-dimethoxybiphenyl): 150 mg (0.365 mmol)
Potassium acetate: 0.895 g (9.12 mmol)
1,4-dioxane (dehydrated): 24 mL Next, the reaction solution was processed by nitrogen bubbling for 10 minutes, then heated for 2.5 hours at 115° C. with stirring under nitrogen. After the reaction solution was then cooled to room temperature, the reaction solution was diluted by addition of toluene to generate a salt, and this salt was removed by filtration. The filtrate was washed with a saturated aqueous sodium chloride solution and was then dried over sodium sulfate. The filtrate thus processed was then concentrated under reduced pressure, so that a crude product was obtained. This crude product was then purified by a silica gel column chromatography (eluent: toluene/heptane=3/2), so that 1.32 g (yield: 86%) of InPTBpin-1 was obtained.

(3) Synthesis of Example Compound A211

[Chem. 18]

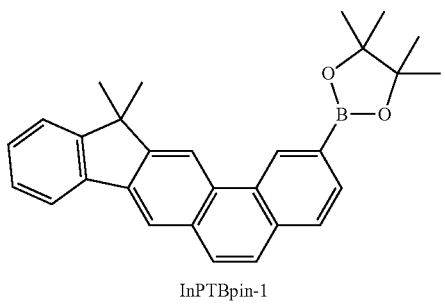 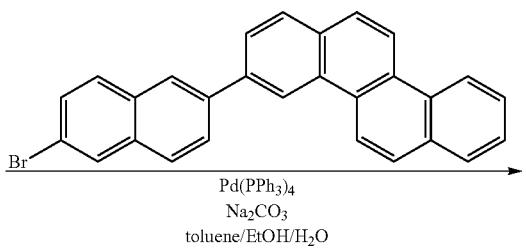

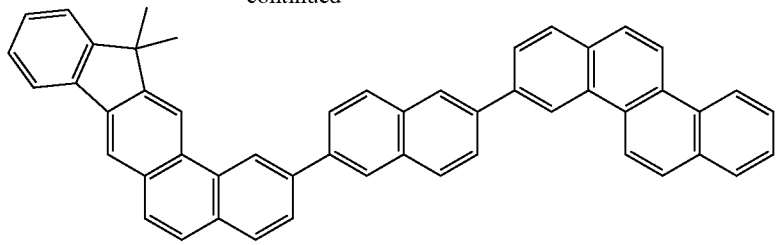

A211

The following reagents and solvents were charged into a 100-ml recovery flask.
InPTBpin-1: 500 mg (1.19 mmol)
3-(6-bromonaphthalen-2-yl)chrysene: 491 mg (1.13 mmol)
Tetrakis(triphenylphosphine)palladium(0): 39 mg (34 μmol)
Toluene: 16 mL
Ethanol: 8 mL
10-wt % aqueous sodium carbonate solution: 8 mL

[Chem. 19]

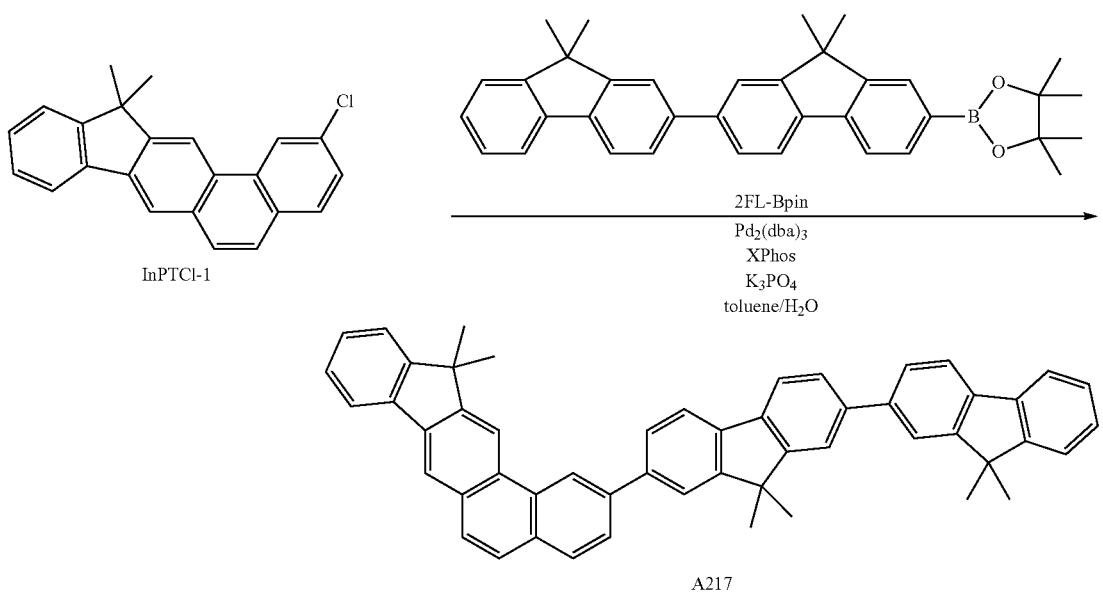

Next, the reaction solution was refluxed by heating for 4 hours with stirring under nitrogen. After the reaction was completed, a crystal precipitated by addition of water to the reaction solution and by stirring thereof was obtained by filtration and was then washed with water and ethanol in this order, so that a crude product was obtained. After this crude product was dissolved by heating using 120 mL of xylene, hot gel filtration was performed using a small amount of silica gel. Subsequently, after the filtrate was concentrated under reduced pressure, recrystallization from xylene/heptane was performed, and a crystal obtained thereby was vacuum-dried at 150° C., so that 561 mg (yield: 77%) of an example compound A211 was obtained.

Next, sublimation purification was performed at $1 \times 10^{-4}$ Pa and 385° C., so that 256 mg of a highly purified example compound A211 was obtained.

The compound thus obtained was identified by a mass spectroscopy measurement.

[MALDI-TOF-MS]
Observed value: m/z=646.454, calculated value: $C_{51}H_{34}$=646.266

Example 2

Synthesis of Example Compound A217

The following reagents and solvents were charged into a nitrogen-replaced 100-ml recovery flask.
InPTCl-1: 700 mg (2.13 mmol)
2FL-Bpin: 1.14 g (2.24 mmol)
Tris(dibenzylideneacetone)dipalladium(0): 97 mg (0.106 mmol)
XPhos (2-dicyclohexylphosphino-2',4',6'-triisopropylbiphenyl): 152 mg (0.319 mmol)
Potassium phosphate: 1.35 g (6.39 mmol)
Toluene: 36 mL
Water: 1 mL Next, the reaction solution was processed by nitrogen bubbling for 10 minutes, then heated for 3 hours at 110° C. with stirring under nitrogen. After the reaction was completed, and toluene and water were then added to the reaction, stirring was further performed, and an organic layer was then separated by a liquid separation operation. This organic layer was then washed with a saturated aqueous sodium chloride solution and was further dried over sodium sulfate. The organic layer was then concentrated under reduced pressure, so that a crude product was obtained. This crude product was then purified by a silica gel column chromatography (eluent: heptane/chloroform=3/1). Furthermore, a crystal obtained by recrystallization from toluene/heptane was vacuum-dried at 150° C., so that 1.28 g (yield: 88%) of an example compound A217 was obtained. Subsequently, a part of the compound thus obtained was processed by sublimation purification at $1\times10^{-4}$ Pa and 360° C., so that 845 mg of a highly purified example compound A217 was obtained.

The compound thus obtained was identified by a mass spectroscopy measurement.

[MALDI-TOF-MS]

Observed value: m/z=678.519, calculated value: $C_{53}H_{42}$=678.329

Example 3

Synthesis of Example Compound A205

[Chem. 20]

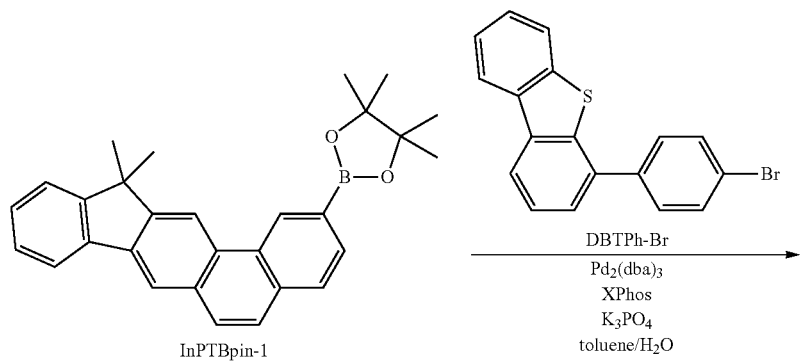

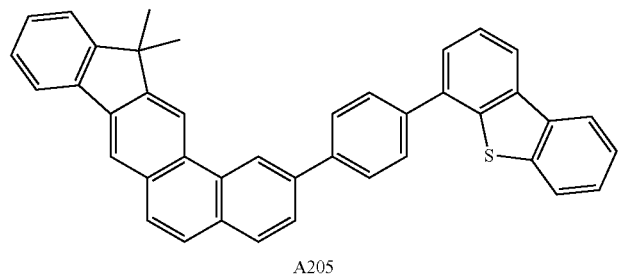

The following reagents and solvents were charged into a 100-mL recovery flask.
InPTBpin-1: 300 mg (0.714 mmol)
DBTPh-Br: 263 mg (0.680 mmol)
Tetrakis(triphenylphosphine)palladium(0): 24 mg (20 μmol)
Toluene: 10 mL
Ethanol: 5 mL
10 wt %-aqueous sodium carbonate solution: 5 mL Next, the reaction solution was refluxed by heating for 4 hours with stirring under nitrogen. After the reaction was completed, to the reaction solution was added toluene and water and the mixture was stirred, and an organic layer was then separated by a liquid separation operation. Next, after being washed with a saturated aqueous sodium chloride solution, the organic layer was dried over sodium sulfate. The organic layer was then concentrated under reduced pressure, so that a crude product was obtained. This crude product was purified by a silica gel column chromatography (eluent: heptane/chloroform=3/1) and was then further purified by recrystallization from toluene/heptane. Subsequently, the crystal thus obtained was vacuum-dried at 150° C., so that 267 mg (yield: 71%) of an example compound A205 was obtained.

Next, sublimation purification was performed at $1\times10^{-4}$ Pa and 340° C., so that 160 mg of a highly purified example compound A205 was obtained.

The compound thus obtained was identified by a mass spectroscopy measurement.

[MALDI-TOF-MS]

Observed value: m/z=552.375, calculated value: $C_{41}H_{28}S$=552.191

Example 4

Synthesis of Example Compound A309

[Chem. 21]

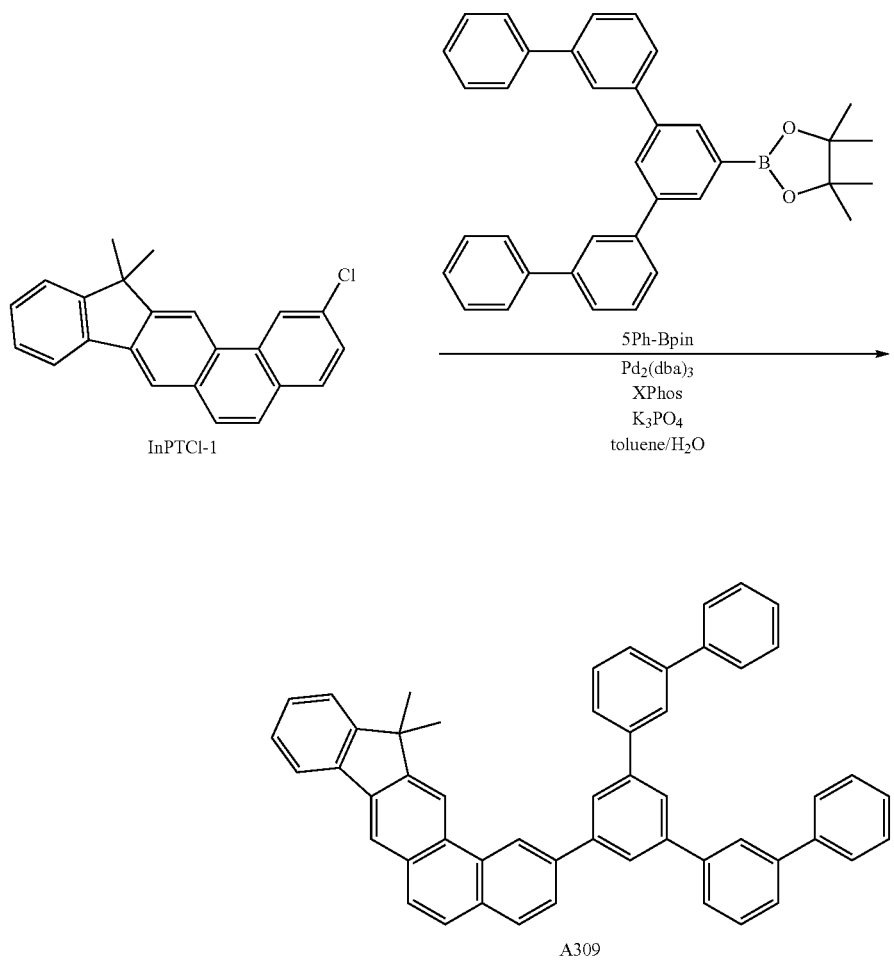

The following reagents and solvents were charged into a nitrogen-replaced 50-mL recovery flask.
InPTCl-1: 300 mg (0.912 mmol)
5Ph-Bpin: 478 mg (0.940 mmol)
Tris(dibenzylideneacetone)dipalladium(0): 97 mg (0.106 mmol)
XPhos: 66 mg (0.138 mmol)
Potassium phosphate: 581 mg (2.73 mmol)
Toluene: 15 mL
Water: 0.3 mL Next, the reaction solution was processed by nitrogen bubbling for 10 minutes, then heated for 5 hours at 110° C. with stirring under nitrogen. After the reaction was completed, to the reaction solution was added toluene and water and the mixture was stirred, and an organic layer was then separated by a liquid separation operation. Next, after being washed with a saturated aqueous sodium chloride solution, the organic layer was dried over sodium sulfate. The organic layer was then concentrated under reduced pressure, so that a crude product was obtained. This crude product was purified by a silica gel column chromatography (eluent: heptane/chloroform=2/1) and was then further purified by recrystallization from toluene/heptane. Subsequently, the crystal thus obtained was vacuum-dried at 150° C., so that 490 mg (yield: 80%) of an example compound A309 was obtained.

Next, sublimation purification was performed at $1\times10^{-4}$ Pa and 390° C., so that 315 mg of a highly purified example compound A309 was obtained.

The compound thus obtained was identified by a mass spectroscopy measurement.

[MALDI-TOF-MS]
Observed value: m/z=674.502, calculated value: $C_{53}H_{38}$=674.297

Example 5

Synthesis of Example Compound A402

[Chem. 22]

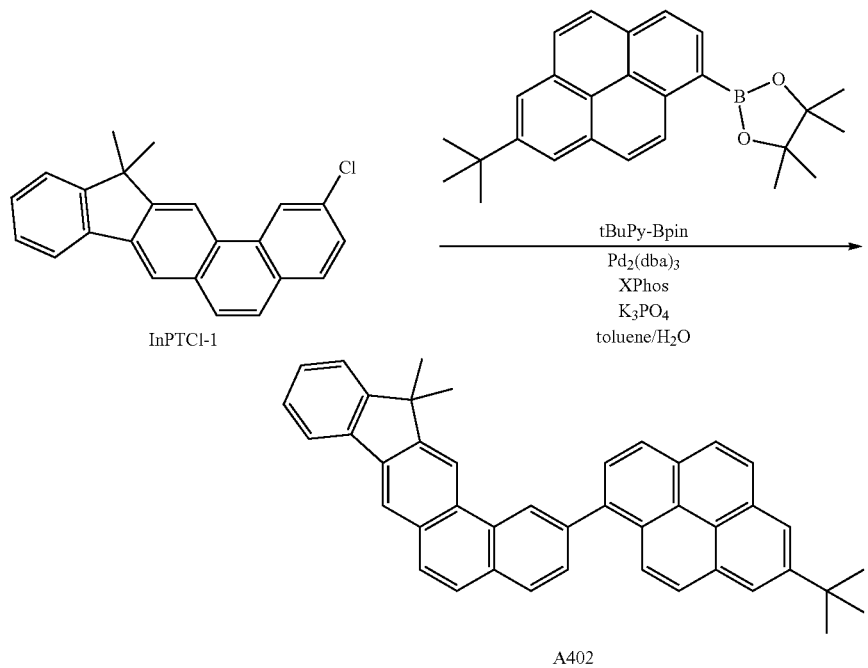

A402

The following reagents and solvents were charged into a nitrogen-replaced 50-mL recovery flask.
InPTCl-1: 300 mg (0.912 mmol)
tBuPy-Bpin: 361 mg (0.940 mmol)
Tris(dibenzylideneacetone)dipalladium(0): 97 mg (0.106 mmol)
XPhos: 66 mg (0.138 mmol)
Potassium phosphate: 581 mg (2.73 mmol)
Toluene: 15 mL
Water: 0.3 mL Next, the reaction solution was processed by nitrogen bubbling for 10 minutes, then heated for 4 hours at 110° C. with stirring under nitrogen. After the reaction was completed, to the reaction solution was added toluene and water and the mixture was stirred, and an organic layer was then separated by a liquid separation operation. Next, after being washed with a saturated aqueous sodium chloride solution, the organic layer was dried over sodium sulfate. The organic layer was then concentrated under reduced pressure, so that a crude product was obtained. This crude product was purified by a silica gel column chromatography (eluent: heptane/chloroform=2/1) and was then further purified by recrystallization from toluene/heptane. Subsequently, the crystal thus obtained was vacuum-dried at 150° C., so that 414 mg (yield: 82%) of an example compound A402 was obtained.

Next, sublimation purification was performed at $1 \times 10^{-4}$ Pa and 360° C., so that 280 mg of a highly purified example compound A402 was obtained.

The compound thus obtained was identified by a mass spectroscopy measurement.

[MALDI-TOF-MS]
Observed value: m/z=550.458, calculated value: $C_{43}H_{34}$=550.266

Example 6

Synthesis of Example Compound A115

[Chem. 23]

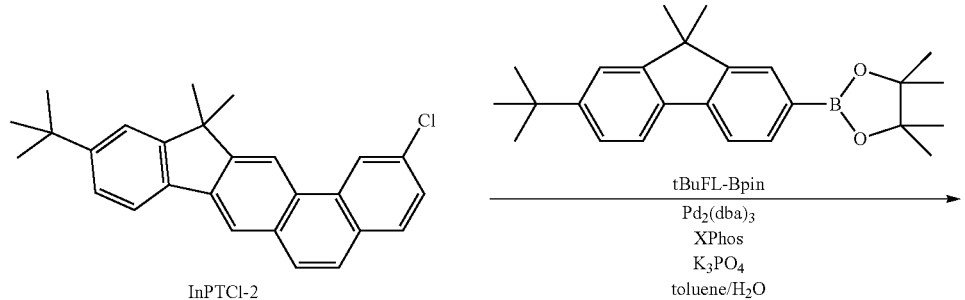

-continued

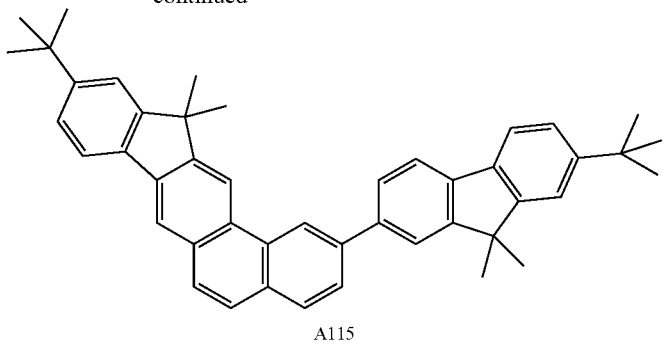

A115

(1) Synthesis of InPTCl-2

InPTCl-2 was synthesized by a method similar to that of Example 1(1) except that tBuPL-Bpin was used instead of FL-Bpin used in Example 1(1).

(2) Synthesis of Example Compound A115

The following reagents and solvents were charged into a nitrogen-replaced 50-mL recovery flask.

InPTCl-2: 250 mg (0.649 mmol)
tBuPy-Bpin: 252 mg (0.668 mmol)
Tris(dibenzylideneacetone)dipalladium(0): 30 mg (32 μmol)
XPhos: 46 mg (96 μmol)
Potassium phosphate: 413 mg (1.95 mmol)
Toluene: 12 mL
Water: 0.3 mL Next, the reaction solution was processed by nitrogen bubbling for 10 minutes, then heated for 5 hours at 110° C. with stirring under nitrogen. After the reaction was completed, to the reaction solution was added toluene and water and the mixture was stirred, and an organic layer was then separated by a liquid separation operation. Next, after being washed with a saturated aqueous sodium chloride solution, the organic layer was dried over sodium sulfate. The organic layer was then concentrated under reduced pressure, so that a crude product was obtained. This crude product was purified by a silica gel column chromatography (eluent: heptane/chloroform=3/1) and was then further purified by recrystallization from toluene/heptane. Subsequently, the crystal thus obtained was vacuum-dried at 130° C., so that 297 mg (yield: 76%) of an example compound A115 was obtained.

Next, sublimation purification was performed at $1 \times 10^{-4}$ Pa and 350° C., so that 190 mg of a highly purified example compound A115 was obtained.

The compound thus obtained was identified by a mass spectroscopy measurement.

[MALDI-TOF-MS]

Observed value: m/z=598.561, calculated value: $C_{46}H_{46}$=598.360

Example 7

In this example, an organic light emitting element having the structure in which an anode, a hole transport layer, an electron blocking layer, a light emitting layer, a hole blocking layer, an electron transport layer, and a cathode were sequentially provided on a substrate was formed by the following method. Some of materials used in this example are shown below.

[Chem. 24]

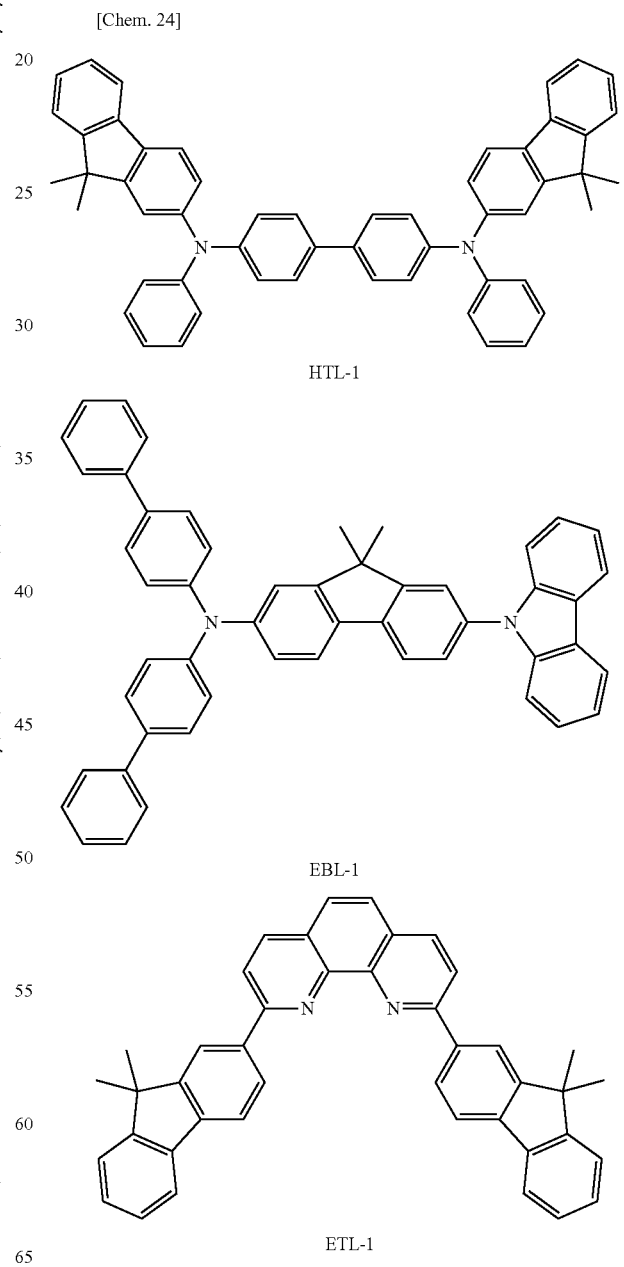

HTL-1

EBL-1

ETL-1

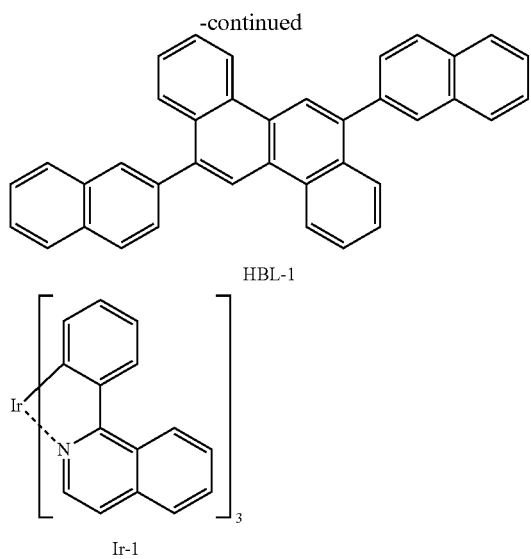

HBL-1

Ir-1

A film of an indium zinc oxide was formed as the anode on a glass substrate by a sputtering method. The thickness of the anode in this case was set to 100 nm. As described above, the substrate provided with the anode was used as a transparent conductive substrate (substrate with anode) in the following steps.

Next, on this transparent conductive substrate, the following organic compound layers and electrode layers were successively formed by vacuum deposition performed in a vacuum chamber at a pressure of $1\times10^{-5}$ Pa using resistance heating. In this step, the areas of the electrodes facing each other were each set to 3 mm².

TABLE 3

| | MATERIALS | FILM THICKNESS [nm] |
|---|---|---|
| HOLE TRANSPORT LAYER | HTL-1 | 50 |
| ELECTRON BLOCKING LAYER | EBL-1 | 10 |
| LIGHT EMITTING LAYER | HOST: EXAMPLE COMPOUND A115 GUEST: Ir-1 (Content of guest is 4 vol % of total light emitting layer) | 30 |
| HOLE BLOCKING LAYER | HBL-1 | 10 |
| ELECTRON TRANSPORT LAYER | ETL-1 | 50 |
| FIRST METAL ELECTRODE LAYER | LiF | 0.5 |
| SECOND METAL ELECTRODE LAYER | Al | 100 |

Next, in order to prevent element degradation of the organic light emitting element caused by adsorption of moisture thereto, the organic light emitting element was covered with a protective glass plate and was then sealed with an acrylic resin adhesive in a dry air atmosphere. As described above, the organic light emitting element was obtained.

In the organic light emitting element thus obtained, when the indium zinc oxide electrode was used as the anode, the Al electrode was used as the cathode, and a voltage of 5.5 V was applied thereto, red light emission having a luminance of 1,000 cd/m² and an external quantum efficiency of 13.9% was observed. In addition, the CIE chromaticity coordinates were (x, y)=(0.68, 0.32). Furthermore, in this organic light emitting element, a luminance half-life at a constant current density of 100 mA/cm² was 910 hours.

Examples 8 to 11 and Comparative Examples 1 and 2

An organic light emitting element was formed by a method similar to that of Example 7 except that the compounds used in Example 7 as constituent materials of the electron blocking layer, the light emitting layer, and the hole blocking layer were changed to the compounds shown in the following Table 4. Some of materials used in Examples 8 to 11 and Comparative Examples 1 and 2 are shown below.

[Chem. 25]

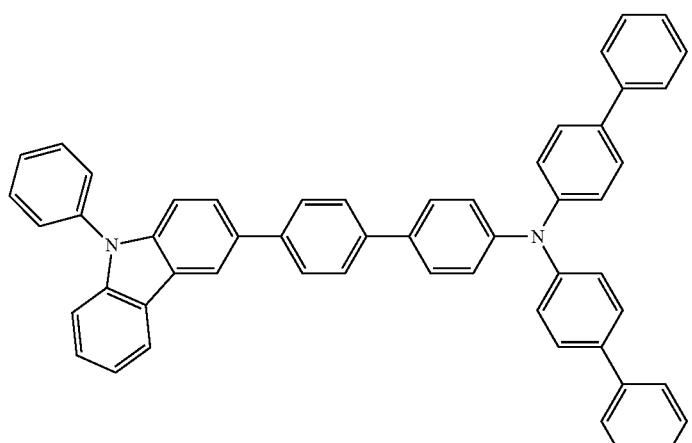

EBL-2

-continued

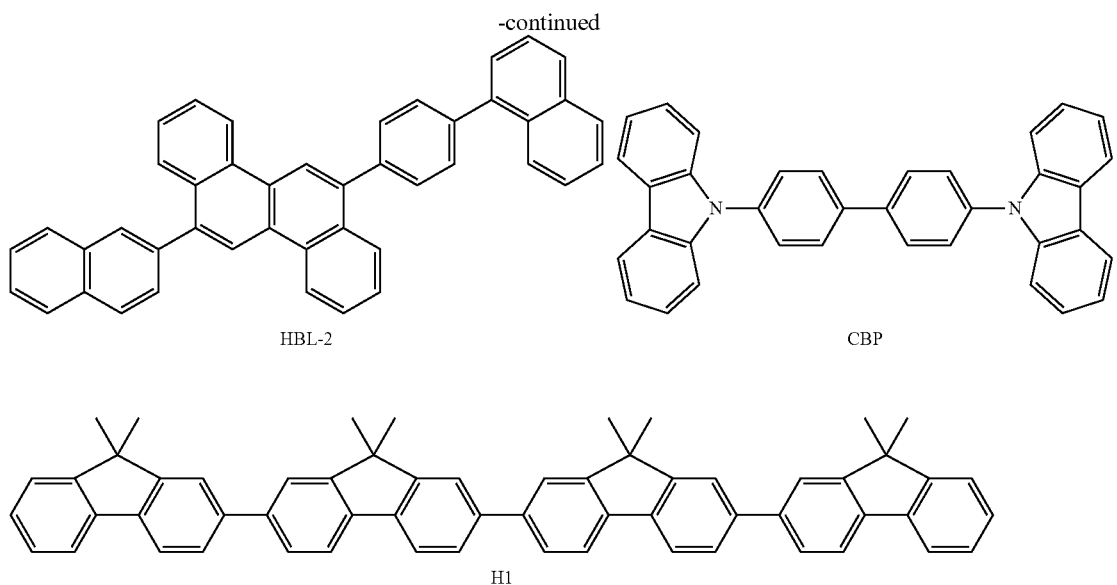

HBL-2 CBP

H1

In addition, the organic light emitting element thus obtained was evaluated by a method similar to that of Example 7. The results are shown in Table 4.

TABLE 4

| | ELECTRON BLOCKING LAYER | LIGHT EMITTING LAYER HOST | LIGHT EMITTING LAYER GUEST | HOLE BLOCKING LAYER | CIE CHROMATICITY | @1000 cd/m² | | LUMINANCE HALF-LIFE @100 mA/cm² (hr) |
|---|---|---|---|---|---|---|---|---|
| | | | | | | APPLIED VOLTAGE (V) | EXTERNAL QUANTUM EFFICIENCY (%) | |
| EXAMPLE 7 | EBL-1 | EXAMPLE COMPOUND A115 | Ir-1 | HBL-1 | 0.68, 0.32 | 5.5 | 13.9 | 910 |
| EXAMPLE 8 | EBL-1 | EXAMPLE COMPOUND A205 | Ir-1 | HBL-2 | 0.68, 0.32 | 5.6 | 14.5 | 1180 |
| EXAMPLE 9 | EBL-2 | EXAMPLE COMPOUND A211 | Ir-1 | HBL-1 | 0.68, 0.32 | 5.4 | 14.0 | 1750 |
| EXAMPLE 10 | EBL-2 | EXAMPLE COMPOUND A217 | Ir-1 | HBL-1 | 0.68, 0.32 | 5.2 | 14.2 | 1610 |
| EXAMPLE 11 | EBL-1 | EXAMPLE COMPOUND A309 | Ir-1 | HBL-2 | 0.68, 0.32 | 6.2 | 13.7 | 1290 |
| COMPARATIVE EXAMPLE 1 | EBL-1 | COMPARATIVE COMPOUND CBP | Ir-1 | HBL-1 | 0.68, 0.32 | 6.9 | 9.1 | 100 |
| COMPARATIVE EXAMPLE 2 | EBL-2 | COMPARATIVE COMPOUND H1 | Ir-1 | HBL-2 | 0.68, 0.32 | 5.8 | 13.5 | 180 |

As described above, when the indeno[1,2-b]phenanthrene compound of the present invention was used in particular, as the host of the light emitting layer of the organic light emitting element, a light emitting element having a high efficiency and an excellent life performance can be obtained. The reason for this is that since a HOMO sparse moiety is present in a molecular structure of the compound of the present invention, and the hole transport property thereof is suppressed as compared to that of the comparative compounds CBP and H1, each of which has no HOMO sparse moiety, the carrier balance in the light emitting layer is improved.

Example 12

In this example, an organic light emitting element having the structure in which an anode, a hole transport layer, an electron blocking layer, a light emitting layer, a hole blocking layer, an electron transport layer, and a cathode were sequentially provided on a substrate was formed by the following method. Some of materials used in this example are shown below.

[Chem. 26]

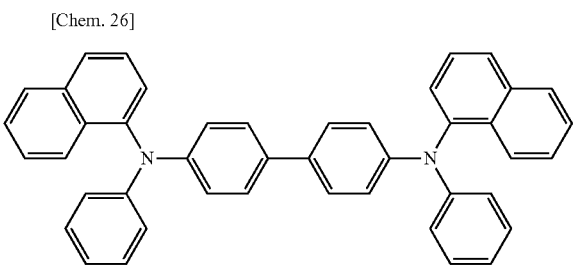

HTL-2

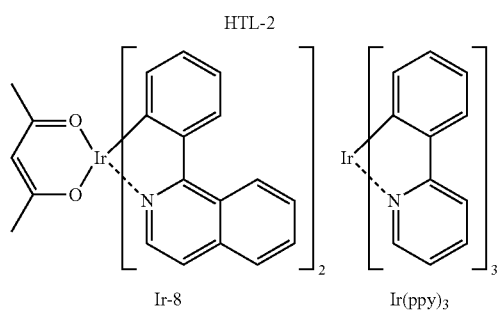

Ir-8          Ir(ppy)₃

A transparent conductive substrate was formed by a method similar to that of Example 7. Next, the following organic compound layers and electrode layers were successively formed on this transparent conductive substrate by vacuum deposition performed in a vacuum chamber at a pressure of 1×10⁻⁵ Pa using resistance heating. In this step, the areas of the electrodes facing each other were each set to 3 mm².

TABLE 5

| | MATERIALS | FILM THICKNESS [nm] |
|---|---|---|
| HOLE TRANSPORT LAYER | HTL-2 | 50 |
| ELECTRON BLOCKING LAYER | EBL-2 | 10 |
| LIGHT EMITTING LAYER | HOST: EXAMPLE COMPOUND A211 GUEST: Ir-8 ASSIST MATERIAL: Ir(ppy)₃ (Contents of guest and assist material are 4 and 16 vol % of total light emitting layer, respectively) | 30 |
| HOLE BLOCKING LAYER | HBL-1 | 10 |
| ELECTRON TRANSPORT LAYER | ETL-1 | 50 |
| FIRST METAL ELECTRODE LAYER | LiF | 0.5 |
| SECOND METAL ELECTRODE LAYER | Al | 100 |

Next, in order to prevent element degradation of the organic light emitting element caused by adsorption of moisture thereto, the organic light emitting element was covered with a protective glass plate and was then sealed with an acrylic resin adhesive in a dry air atmosphere. As described above, the organic light emitting element was obtained.

In the organic light emitting element thus obtained, when the indium zinc oxide electrode was used as the anode, the Al electrode was used as the cathode, and a voltage of 5.9 V was applied thereto, red light emission having a luminance of 2,000 cd/m² and an external quantum efficiency of 18.4% was observed. In addition, in this element, the CIE chromaticity coordinates were (x, y)=(0.68, 0.31). Furthermore, in this light emitting element, a luminance half-life at a constant current density of 100 mA/cm² was 1,460 hours.

Example 13 and Comparative Example 3

An element was formed by a method similar to that of Example 12 except that the compounds used for the light emitting layer in Example 1 were changed to the compounds shown in the following Table 6. In addition, the organic light emitting element thus obtained was evaluated by a method similar to that of Example 7. The results are shown in Table 6.

TABLE 6

| | LIGHT EMITTING LAYER HOST | LIGHT EMITTING LAYER GUEST | LIGHT EMITTING LAYER ASSIST | CIE CHROMATICITY | APPLIED VOLTAGE (V) | EXTERNAL QUANTUM EFFICIENCY (%) | LUMINANCE HALF-LIFE @100 mA/cm² (hr) |
|---|---|---|---|---|---|---|---|
| | | | | | @2000 cd/m² | | |
| EXAMPLE 12 | EXAMPLE COMPOUND A211 | Ir-8 | Ir(ppy)₃ | 0.68, 0.31 | 5.9 | 18.4 | 1460 |
| EXAMPLE 13 | EXAMPLE COMPOUND A217 | Ir-8 | Ir(ppy)₃ | 0.68, 0.31 | 5.7 | 18.5 | 1600 |
| COMPARATIVE EXAMPLE 3 | COMPARATIVE COMPOUND H1 | Ir-8 | Ir(ppy)₃ | 0.68, 0.31 | 6.3 | 17.5 | 330 |

As described above, also in the phosphorescent light emitting element using a light emitting assistant material in the light emitting layer, when the indeno[1,2-b]phenanthrene compound of the present invention was used, a light emitting element having a high efficiency and an excellent life performance can be obtained. The reason for this is that since a HOMO sparse moiety is present in a molecular structure of the compound of the present invention, and the hole transport property thereof is suppressed as compared to that of the comparative compound H1 which has no HOMO sparse moiety, the carrier balance in the light emitting layer is improved.

Example 14

In this example, an organic light emitting element having the structure in which an anode, a hole transport layer, an electron blocking layer, a light emitting layer, a hole blocking layer, an electron transport layer, and a cathode were sequentially provided on a substrate was formed by the following method. Some of materials used in this example are shown below.

[Chem. 27]

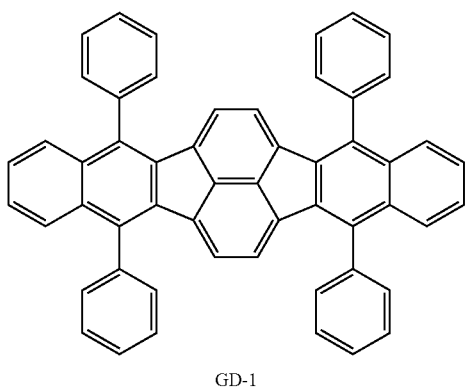

GD-1

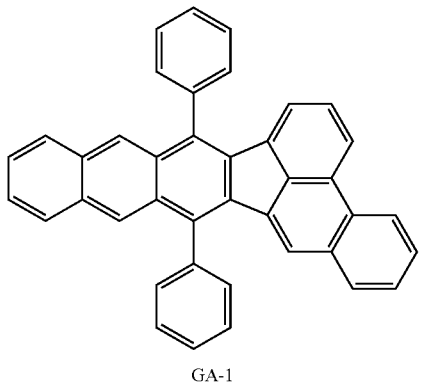

GA-1

First, a transparent conductive substrate was formed by a method similar to that of Example 7. Next, the following organic compound layers and electrode layers were successively formed on this transparent conductive substrate by vacuum deposition performed in a vacuum chamber at a pressure of $1 \times 10^{-5}$ Pa using resistance heating. In this case, the areas of the electrodes facing each other were each set to 3 mm$^2$.

TABLE 7

| | MATERIALS | FILM THICKNESS [nm] |
|---|---|---|
| HOLE TRANSPORT LAYER | HTL-1 | 40 |
| ELECTRON BLOCKING LAYER | EBL-1 | 10 |
| LIGHT EMITTING LAYER | HOST: EXAMPLE COMPOUND A402 GUEST: GD-1 ASSIST MATERIAL: GA-1 (Contents of guest and assist material are 1 and 35 vol % of total light emitting layer, respectively) | 30 |
| HOLE BLOCKING LAYER | HBL-1 | 10 |
| ELECTRON TRANSPORT LAYER | ETL-1 | 50 |
| FIRST METAL ELECTRODE LAYER | LiF | 0.5 |
| SECOND METAL ELECTRODE LAYER | Al | 100 |

Next, in order to prevent element degradation of the organic light emitting element caused by adsorption of moisture thereto, the organic light emitting element was covered with a protective glass plate and was then sealed with an acrylic resin adhesive in a dry air atmosphere. As described above, the organic light emitting element was obtained.

In the organic light emitting element thus obtained, when the indium zinc oxide electrode was used as the anode, the Al electrode was used as the cathode, and a voltage of 4.0 V was applied thereto, green light emission having a light emitting efficiency of 23.0 cd/A and a luminance of 2,000 cd/m$^2$ was observed. In addition, in this element, the CIE chromaticity coordinates were (x, y)=(0.21, 0.69). Furthermore, in this light emitting element, a luminance half-life at a constant current density of 100 mA/cm$^2$ was 2,630 hours.

Comparative Example 4

An organic light emitting element was formed in a manner similar to that of Example 14 except that the compound used for the light emitting layer in Example 14 was changed to the compound shown in the following Table 8. In addition, the organic light emitting element thus formed was evaluated by a method similar to that of Example 7. The results are shown in Table 8.

TABLE 8

| | LIGHT EMITTING LAYER HOST | LIGHT EMITTING LAYER GUEST | LIGHT EMITTING LAYER ASSIST | CIE CHROMATICITY | APPLIED VOLTAGE (V) | @2000 cd/m² EXTERNAL QUANTUM EFFICIENCY (cd/A) | LUMINANCE HALF-LIFE @100 mA/cm² |
|---|---|---|---|---|---|---|---|
| EXAMPLE 14 | COMPARATIVE COMPOUND A402 | GD-1 (1 vol %) | GA-1 (35 vol %) | 0.21, 0.69 | 4.0 | 23.0 | 2630 |
| COMPARATIVE EXAMPLE 4 | COMPARATIVE COMPOUND H1 | GD-1 (1 vol %) | GA-1 (35 vol %) | 0.21, 0.69 | 4.8 | 18.1 | 1700 |

From the above results, it is found that even if the fluorescent light emitting material is used as the guest of the light emitting layer, by the use of the indeno[1,2-b]phenanthrene compound of the present invention as the host of the light emitting layer, an element having a high efficiency and a long life can be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-222890, filed Oct. 5, 2012, which is hereby incorporated by reference herein in its entirety.

Industrial Applicability

As has thus been described, the indeno[1,2-b]phenanthrene compound of the present invention is a compound designed to improve the carrier balance in a light emitting layer, and as the structural characteristic of this indeno[1,2-b]phenanthrene compound, a HOMO sparse moiety is present in the molecular structure thereof. Accordingly, the indeno[1,2-b]phenanthrene compound of the present invention is a compound having a suppressed hole transport property. Hence, when the compound of the present invention is used as a constituent material of an organic light emitting element, in particular, as a host of a light emitting layer, and in more particular as a host of a light emitting layer included in a red phosphorescent light emitting element, the organic light emitting element becomes an organic light emitting element having a high efficiency and an excellent life performance.

REFERENCE SIGNS LIST

18: TFT element, 21: anode, 22: organic compound layer, 23: cathode

The invention claimed is:

1. An indeno[1,2-b]phenanthrene compound represented by the following general formula [1]:

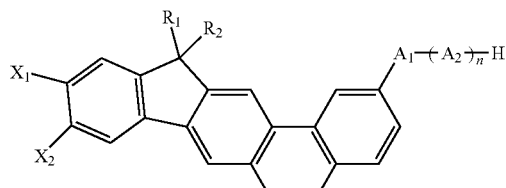

[1]

wherein in the formula [1], $R_1$ and $R_2$ each represent a hydrogen atom or an alkyl group;

$X_1$ and $X_2$ each represent a substitute selected from the group consisting of a hydrogen atom, an alkyl group, a methoxy group, and a cyano group;

$A_1$ represents a monovalent or a divalent aromatic hydrocarbon group, and $A_1$ is optionally substituted by an alkyl group, a phenyl group optionally further substituted by an alkyl group, or a biphenyl group optionally further substituted by an alkyl group;

$A_2$ represents a monovalent or a divalent aromatic hydrocarbon group or a monovalent or a divalent heteroaromatic group, and $A_2$ is optionally substituted by an alkyl group, a phenyl group optionally further substituted by an alkyl group, or a biphenyl group optionally further substituted by an alkyl group;

n represents an integer of 0 to 4; and when n is 2 or more, a plurality of $A_2$ are identical to or different from each other.

2. The indeno[1,2-b]phenanthrene compound according to claim 1, wherein $X_1$ and $X_2$ each represent a hydrogen atom.

3. The indeno[1,2-b]phenanthrene compound according to claim 1, wherein n is 0 or 1.

4. The indeno[1,2-b]phenanthrene compound according to claim 1, wherein the indeno[1,2-b]phenanthrene compound is a compound represented by the following general formula [2]:

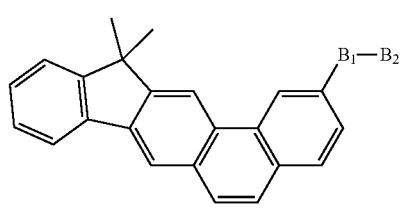

[2]

wherein in the formula [2], $B_1$ represents a divalent aromatic hydrocarbon group, $B_2$ represents a monovalent aromatic hydrocarbon group or a monovalent heteroaromatic group, and $B_1$ and $B_2$ are each optionally substituted by an alkyl group.

5. The indeno[1,2-b]phenanthrene compound according to claim 4, wherein $B_1$ is selected from the following divalent substituents:

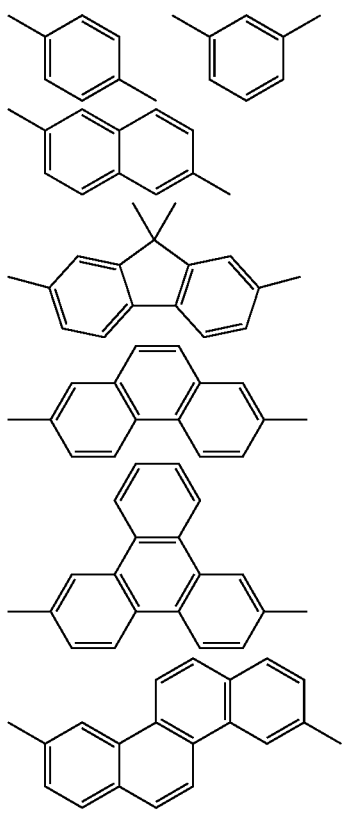

6. An organic light emitting element comprising:
a pair of electrodes; and
an organic compound layer arranged between the pair of electrodes,
wherein the organic compound layer contains the indeno[1,2-b]phenanthrene compound according to claim 1.

7. The organic light emitting element according to claim 6, wherein the organic compound layer is a light emitting layer.

8. The organic light emitting element according to claim 7, wherein the light emitting layer includes a host and a guest, and
the host includes the indeno[1,2-b]phenanthrene compound.

9. The organic light emitting element according to claim 8, wherein the guest includes a phosphorescent light emitting material.

10. The organic light emitting element according to claim 9, wherein the phosphorescent light emitting material includes an iridium complex.

11. The organic light emitting element according to claim 6, wherein the light emitting layer includes a plurality of light emitting materials,
one of the light emitting materials is an organic compound represented by the general formula [1], and
the light emitting layer emits white light.

12. A display device comprising:
a plurality of pixels;
wherein the pixels each includes the organic light emitting element according to claim 6 and an active element connected to the organic light emitting element.

13. An information processing device comprising:
a display unit to display an image; and
an input unit to input image information,
wherein the display unit includes the display device according to claim 12.

14. A lighting device comprising:
the organic light emitting element according to claim 6; and
an AC/DC converter circuit connected to the organic light emitting element.

15. An image forming device comprising:
a photosensitive body;
a charging unit charging a surface of the photosensitive body;
an exposing unit exposing the photosensitive body to form an electrostatic latent image; and
a developing unit developing the electrostatic latent image formed on the surface of the photosensitive body,
wherein the exposing unit includes the organic light emitting element according to claim 6.

16. An exposure device exposing a photosensitive body, the exposure device comprising a plurality of the organic light emitting elements each according to claim 6,
wherein the organic light emitting elements are arranged to form at least one line.

* * * * *